United States Patent
Le et al.

(10) Patent No.: US 10,245,422 B2
(45) Date of Patent: Apr. 2, 2019

(54) MICROPROJECTION APPLICATORS AND METHODS OF USE

(71) Applicant: CORIUM INTERNATIONAL, INC., Menlo Park, CA (US)

(72) Inventors: Anthony Le, San Jose, CA (US); Doug Bourne, Campbell, CA (US); Ashutosh Shastry, Santa Clara, CA (US); Robert Wade Worsham, Cupertino, CA (US); Parminder Singh, Union City, CA (US)

(73) Assignee: Corium International, Inc., Menlo Park, CA (US)

( * ) Notice: Subject to any disclaimer, the term of this patent is extended or adjusted under 35 U.S.C. 154(b) by 801 days.

(21) Appl. No.: 14/201,644

(22) Filed: Mar. 7, 2014

(65) Prior Publication Data

US 2014/0276580 A1    Sep. 18, 2014

Related U.S. Application Data

(60) Provisional application No. 61/778,274, filed on Mar. 12, 2013.

(51) Int. Cl.
*A61M 37/00* (2006.01)
*A61M 5/158* (2006.01)

(52) U.S. Cl.
CPC . *A61M 37/0015* (2013.01); *A61M 2005/1585* (2013.01); *A61M 2037/0023* (2013.01); *A61M 2037/0046* (2013.01); *A61M 2037/0061* (2013.01)

(58) Field of Classification Search
CPC .. A61M 2005/1585; A61M 2037/0023; A61M 2037/0046; A61M 2037/0061; A61M 37/0015
See application file for complete search history.

(56) References Cited

U.S. PATENT DOCUMENTS

| | | |
|---|---|---|
| 1,554,510 A | 9/1925 | Kirby |
| 1,770,632 A | 7/1930 | Smith |
| 2,046,240 A | 6/1936 | Bayley |
| 2,434,407 A | 1/1948 | George |
| 3,675,766 A | 7/1972 | Rosenthal |
| 3,704,194 A | 11/1972 | Harrier |
| 3,814,097 A | 6/1974 | Ganderton et al. |
| 3,873,255 A | 3/1975 | Kalwaites |
| 3,918,449 A | 11/1975 | Pistor |
| 3,964,482 A | 6/1976 | Gerstel et al. |

(Continued)

FOREIGN PATENT DOCUMENTS

| | | |
|---|---|---|
| CA | 2205444 | 6/1996 |
| CA | 2376285 | 12/2000 |

(Continued)

OTHER PUBLICATIONS

Avcin et al., "Subcutaneous nodule after vaccination with an aluminum-containing vaccina", Acta Dermatoven, APA, vol. 17. No. 4, pp. 182-184 (2008).

(Continued)

*Primary Examiner* — Brandy S Lee
(74) *Attorney, Agent, or Firm* — McDermott Will & Emery LLP; John M. Mohr

(57) ABSTRACT

Applicators for a microprojection array and methods of using the applicators are described.

23 Claims, 11 Drawing Sheets

(56) References Cited

U.S. PATENT DOCUMENTS

| | | |
|---|---|---|
| 4,055,029 A | 10/1977 | Kalbow |
| 4,117,841 A | 10/1978 | Perrotta et al. |
| 4,151,240 A | 4/1979 | Lucas et al. |
| 4,180,232 A | 12/1979 | Hardigg |
| 4,342,314 A | 8/1982 | Radel et al. |
| 4,381,963 A | 5/1983 | Goldstein et al. |
| 4,395,215 A | 7/1983 | Bishop |
| 4,402,696 A | 9/1983 | Gulko |
| 4,460,368 A | 7/1984 | Allison et al. |
| 4,460,370 A | 7/1984 | Allison et al. |
| 4,463,045 A | 7/1984 | Ahr et al. |
| 4,509,908 A | 4/1985 | Mullane, Jr. |
| 4,515,168 A | 5/1985 | Chester et al. |
| 4,556,441 A | 12/1985 | Faasse, Jr. |
| 4,585,991 A | 4/1986 | Reid et al. |
| 4,597,961 A | 7/1986 | Etscorn |
| 4,609,518 A | 9/1986 | Curro et al. |
| 4,630,603 A | 12/1986 | Greenway |
| 4,660,721 A | 4/1987 | Mykleby |
| 4,695,422 A | 9/1987 | Curro et al. |
| 4,743,234 A | 5/1988 | Leopoldi et al. |
| 4,743,249 A | 5/1988 | Loveland |
| 4,784,737 A | 11/1988 | Ray et al. |
| 4,812,305 A | 3/1989 | Vocal |
| 4,837,049 A | 6/1989 | Byers et al. |
| 4,846,821 A | 7/1989 | Lyons et al. |
| 4,904,475 A | 2/1990 | Gale et al. |
| 4,996,159 A | 2/1991 | Glaser |
| 5,051,259 A | 9/1991 | Olsen et al. |
| 5,061,258 A | 10/1991 | Martz |
| 5,134,079 A | 7/1992 | Cusack et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |
| 5,163,918 A | 11/1992 | Righi et al. |
| 5,190,558 A | 3/1993 | Ito |
| 5,198,192 A | 3/1993 | Saito et al. |
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabineau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,287 A | 6/1996 | Miskinyar |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,569,469 A | 10/1996 | Lovrechich |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Eriksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,868,244 A | 2/1999 | Ivanov et al. |
| 5,873,849 A | 2/1999 | Bernard |
| 5,879,326 A | 3/1999 | Godshall et al. |
| 5,900,252 A | 5/1999 | Calanchi et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | Devillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,038,465 A | 3/2000 | Melton, Jr. |
| 6,038,485 A | 3/2000 | Axelgaard |
| 6,038,659 A | 3/2000 | Ray et al. |
| 6,047,208 A | 4/2000 | Flower |
| 6,050,988 A | 4/2000 | Zuck |
| 6,055,453 A | 4/2000 | Hofmann et al. |
| 6,080,172 A | 6/2000 | Fujiwara et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,136,008 A | 10/2000 | Becker et al. |
| 6,156,336 A | 12/2000 | Bracht |
| 6,169,224 B1 | 1/2001 | Heinecke et al. |
| 6,181,964 B1 | 1/2001 | Hofmann et al. |
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,248,120 B1 | 6/2001 | Wyszogrodzki |
| 6,256,533 B1 | 7/2001 | Yuzhakov et al. |
| 6,293,925 B1 | 9/2001 | Safabash et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |
| 6,375,627 B1 | 4/2002 | Mauze et al. |
| 6,375,870 B1 | 4/2002 | Visovsky et al. |
| 6,375,978 B1 | 4/2002 | Kleiner et al. |
| 6,379,324 B1 | 4/2002 | Gartstein et al. |
| 6,440,096 B1 | 8/2002 | Lastovich et al. |

(56) References Cited

U.S. PATENT DOCUMENTS

| | | |
|---|---|---|
| 6,451,240 B1 | 9/2002 | Sherman et al. |
| 6,471,903 B2 | 10/2002 | Sherman et al. |
| 6,476,288 B1 | 11/2002 | VanRijswijck et al. |
| 6,485,470 B2 | 11/2002 | Hostettler et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,512,626 B1 | 1/2003 | Schmidt |
| 6,516,223 B2 | 2/2003 | Hofmann |
| 6,532,386 B2 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whiston |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho |
| 6,991,809 B2 | 1/2006 | Anderson |
| 7,011,844 B2 | 3/2006 | Gale et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,128,730 B2 | 10/2006 | Marano-Ford et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,419,481 B2 | 9/2008 | Trautman et al. |
| 7,572,405 B2 | 8/2009 | Sherman et al. |
| 7,578,954 B2 | 8/2009 | Gartstein et al. |
| 7,578,985 B2 | 8/2009 | Gartstein et al. |
| 7,611,481 B2 | 11/2009 | Cleary et al. |
| 7,658,728 B2 | 2/2010 | Yuzhakov |
| 7,678,777 B2 | 3/2010 | Yasuda et al. |
| 7,763,203 B2 | 7/2010 | Arias et al. |
| 7,785,301 B2 | 8/2010 | Yuzhakov |
| 7,789,733 B2 | 9/2010 | Sugimura |
| 7,798,987 B2 | 9/2010 | Trautman et al. |
| 7,828,827 B2 | 11/2010 | Gartstein et al. |
| 7,846,488 B2 | 12/2010 | Johnson |
| 7,914,480 B2 | 3/2011 | Cleary et al. |
| 8,057,842 B2 | 11/2011 | Choi et al. |
| 8,062,573 B2 | 11/2011 | Kwon |
| 8,216,190 B2 | 7/2012 | Gartstein et al. |
| 8,267,889 B2 | 9/2012 | Cantor et al. |
| 8,366,677 B2 | 2/2013 | Kaspar et al. |
| 8,696,638 B2 | 4/2014 | Terahara et al. |
| 8,702,726 B2 | 4/2014 | Gartstein et al. |
| 8,734,697 B2 | 5/2014 | Chen et al. |
| 8,747,362 B2 | 6/2014 | Terahara |
| 8,771,781 B2 | 7/2014 | Tokumoto et al. |
| 8,821,446 B2 | 9/2014 | Trautman et al. |
| 8,834,423 B2 | 9/2014 | Falo, Jr. et al. |
| 8,900,180 B2 | 12/2014 | Wolter et al. |
| 8,911,749 B2 | 12/2014 | Ghartey-Tagoe et al. |
| 9,114,238 B2 | 8/2015 | Singh et al. |
| 9,220,678 B2 | 12/2015 | Kendall et al. |
| 9,452,280 B2 | 9/2016 | Singh et al. |
| 9,498,524 B2 | 11/2016 | Ghartey-Tagoe et al. |
| 9,687,640 B2 | 6/2017 | Trautman et al. |
| 9,687,641 B2 | 6/2017 | Singh et al. |
| 2001/0023324 A1 | 9/2001 | Pronovost et al. |
| 2001/0023351 A1 | 9/2001 | Eilers et al. |
| 2002/0006355 A1 | 1/2002 | Whitson |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0123675 A1* | 9/2002 | Trautman ............ A61B 17/205 600/309 |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0188310 A1 | 12/2002 | Seward et al. |
| 2002/0193729 A1 | 12/2002 | Cormier et al. |
| 2002/0193819 A1 | 12/2002 | Porter et al. |
| 2003/0083645 A1 | 5/2003 | Angel et al. |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0195474 A1 | 10/2003 | Down et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0049150 A1 | 3/2004 | Dalton et al. |
| 2004/0062813 A1 | 4/2004 | Cormier et al. |
| 2004/0087893 A1* | 5/2004 | Kwon .................. A61B 17/205 604/46 |
| 2004/0087992 A1 | 5/2004 | Gartstein et al. |
| 2004/0096455 A1 | 5/2004 | Maa et al. |
| 2004/0106904 A1 | 6/2004 | Gonnelli et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |
| 2004/0265365 A1 | 12/2004 | Daddona et al. |
| 2005/0049549 A1 | 3/2005 | Wong et al. |

(56) References Cited

U.S. PATENT DOCUMENTS

| | | |
|---|---|---|
| 2005/0065463 A1 | 3/2005 | Tobinga et al. |
| 2005/0089554 A1 | 4/2005 | Cormier et al. |
| 2005/0090803 A1 | 4/2005 | Sherman et al. |
| 2005/0096586 A1 | 5/2005 | Trautman et al. |
| 2005/0163827 A1 | 7/2005 | Zech et al. |
| 2005/0178760 A1 | 8/2005 | Chang et al. |
| 2005/0197308 A1 | 9/2005 | Dalton et al. |
| 2005/0209565 A1 | 9/2005 | Yuzhakov et al. |
| 2005/0228340 A1 | 10/2005 | Cleary et al. |
| 2005/0256045 A1 | 11/2005 | Amen et al. |
| 2005/0261631 A1* | 11/2005 | Clarke ............ A61K 9/0021 604/173 |
| 2006/0024358 A1 | 2/2006 | Santini et al. |
| 2006/0067943 A1 | 3/2006 | Maa et al. |
| 2006/0076718 A1 | 4/2006 | Sherman et al. |
| 2006/0095061 A1 | 5/2006 | Trautman et al. |
| 2006/0108914 A1 | 5/2006 | Young |
| 2006/0129174 A1 | 6/2006 | Gartstein et al. |
| 2006/0134188 A1 | 6/2006 | Podhaisky et al. |
| 2006/0149297 A1 | 7/2006 | Sherman et al. |
| 2006/0253079 A1 | 11/2006 | McDonough et al. |
| 2007/0027427 A1 | 2/2007 | Trautman et al. |
| 2007/0191761 A1 | 8/2007 | Boone et al. |
| 2007/0255251 A1 | 11/2007 | Panchula et al. |
| 2008/0009811 A1 | 1/2008 | Cantor |
| 2008/0009825 A1 | 1/2008 | Ringsred et al. |
| 2008/0039805 A1 | 2/2008 | Frederickson et al. |
| 2008/0114298 A1 | 5/2008 | Cantor et al. |
| 2008/0125743 A1 | 5/2008 | Yuzhakov |
| 2008/0183144 A1 | 7/2008 | Trautman et al. |
| 2008/0188771 A1* | 8/2008 | Boecker ............ A61B 5/1411 600/583 |
| 2008/0195035 A1 | 8/2008 | Frederickson et al. |
| 2008/0208134 A1 | 8/2008 | Tomono |
| 2008/0208146 A1 | 8/2008 | Brandwein et al. |
| 2008/0214987 A1 | 9/2008 | Xu |
| 2008/0221532 A1 | 9/2008 | Ogawa |
| 2008/0269685 A1 | 10/2008 | Singh et al. |
| 2009/0017210 A1 | 1/2009 | Andrianov et al. |
| 2009/0035446 A1 | 2/2009 | Kwon |
| 2009/0041810 A1 | 2/2009 | Andrianov et al. |
| 2009/0043279 A1 | 2/2009 | Kaspar et al. |
| 2009/0155330 A1 | 6/2009 | Ghartey-Tagoe et al. |
| 2009/0182306 A1 | 7/2009 | Lee et al. |
| 2009/0216215 A1* | 8/2009 | Thalmann ............ A61M 5/158 604/506 |
| 2010/0028390 A1 | 2/2010 | Cleary et al. |
| 2010/0200494 A1 | 8/2010 | Storer et al. |
| 2010/0228203 A1 | 9/2010 | Quan et al. |
| 2010/0247698 A1 | 9/2010 | Zhang et al. |
| 2011/0006458 A1 | 1/2011 | Sagi et al. |
| 2011/0028905 A1 | 2/2011 | Takada |
| 2011/0046638 A1 | 2/2011 | Gartstein et al. |
| 2011/0059150 A1 | 3/2011 | Kendall et al. |
| 2011/0098651 A1 | 4/2011 | Falo et al. |
| 2011/0121486 A1 | 5/2011 | Oh et al. |
| 2011/0160069 A1 | 6/2011 | Corrie et al. |
| 2011/0177139 A1 | 7/2011 | Hyungil et al. |
| 2011/0276027 A1* | 11/2011 | Trautman .......... A61M 37/0015 604/506 |
| 2011/0276028 A1 | 11/2011 | Singh et al. |
| 2011/0280800 A1 | 11/2011 | Wu et al. |
| 2011/0288484 A1 | 11/2011 | Kendall et al. |
| 2011/0288485 A1 | 11/2011 | Tokumoto et al. |
| 2011/0295205 A1* | 12/2011 | Kaufmann ............ A61M 5/158 604/136 |
| 2011/0306853 A1 | 12/2011 | Black et al. |
| 2012/0052120 A1 | 3/2012 | Castor |
| 2012/0123297 A1* | 5/2012 | Brancazio ............ A61B 5/1411 600/576 |
| 2012/0123387 A1 | 5/2012 | Gonzalez et al. |
| 2012/0130306 A1 | 5/2012 | Terahara et al. |
| 2012/0150023 A1 | 6/2012 | Kaspar et al. |
| 2012/0184906 A1 | 7/2012 | McAllister |
| 2012/0330250 A1 | 12/2012 | Kuwahara et al. |
| 2013/0131598 A1 | 5/2013 | Trautman et al. |
| 2013/0287832 A1 | 10/2013 | O'Hagan et al. |
| 2013/0292868 A1 | 11/2013 | Singh et al. |
| 2013/0292886 A1 | 11/2013 | Sagi et al. |
| 2013/0303502 A1 | 11/2013 | Cavanagh et al. |
| 2014/0148846 A1 | 5/2014 | Pereira et al. |
| 2014/0180201 A1 | 6/2014 | Ding et al. |
| 2014/0248312 A1 | 9/2014 | Rappuoli et al. |
| 2014/0257188 A1 | 9/2014 | Kendall et al. |
| 2014/0272101 A1 | 9/2014 | Chen et al. |
| 2014/0276366 A1 | 9/2014 | Bourne et al. |
| 2014/0276378 A1 | 9/2014 | Chen et al. |
| 2014/0276474 A1 | 9/2014 | Ding et al. |
| 2014/0276580 A1 | 9/2014 | Le et al. |
| 2014/0276589 A1 | 9/2014 | Bayramov et al. |
| 2015/0079133 A1 | 3/2015 | Ghartey-Tagoe et al. |
| 2015/0238413 A1 | 8/2015 | Mochizuki et al. |
| 2015/0297878 A1 | 10/2015 | Singh et al. |
| 2016/0058992 A1 | 3/2016 | Chen et al. |
| 2016/0067176 A1 | 3/2016 | Ding et al. |
| 2016/0135895 A1 | 5/2016 | Faasse et al. |
| 2016/0175572 A1 | 6/2016 | Crowley et al. |
| 2016/0374939 A1 | 12/2016 | Shastry et al. |
| 2017/0281535 A1 | 10/2017 | Singh et al. |

FOREIGN PATENT DOCUMENTS

| | | |
|---|---|---|
| CA | 2316534 | 3/2001 |
| CA | 2422907 | 4/2002 |
| CA | 2889500 A1 | 5/2014 |
| CN | 102000020 A | 6/2011 |
| CN | 102580232 A | 7/2012 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |
| EP | 0301599 | 2/1989 |
| EP | 0305123 A1 | 3/1989 |
| EP | 0312662 | 4/1989 |
| EP | 0400249 | 12/1990 |
| EP | 0407063 | 1/1991 |
| EP | 0796128 | 9/1997 |
| EP | 1086718 A1 | 3/2001 |
| EP | 1086719 A1 | 3/2001 |
| EP | 1174078 | 1/2002 |
| EP | 2283809 A1 | 2/2011 |
| EP | 2399624 A1 | 12/2011 |
| FR | 2535602 | 5/1984 |
| GB | 0783479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-147229 | 5/2000 |
| JP | 2000145777 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |

(56) References Cited

FOREIGN PATENT DOCUMENTS

| | | |
|---|---|---|
| JP | 2001-004442 | 1/2001 |
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-000728 A | 1/2002 |
| JP | 2002-079499 | 3/2002 |
| JP | 2002-151395 | 5/2002 |
| JP | 2002-239014 | 8/2002 |
| JP | 2002301698 | 10/2002 |
| JP | 2003-039399 | 2/2003 |
| JP | 2003-048160 | 2/2003 |
| JP | 2003-534881 A | 11/2003 |
| JP | 2004-065776 A | 3/2004 |
| JP | 2007-190112 A | 1/2006 |
| JP | 2006/271781 A | 10/2006 |
| JP | 2006-341089 A | 12/2006 |
| JP | 2007-130030 A | 5/2007 |
| JP | 2007-536988 A | 12/2007 |
| JP | 2008-006178 A | 1/2008 |
| JP | 2008-074763 A | 4/2008 |
| JP | 2008-194288 A | 8/2008 |
| JP | 2009-082206 A | 4/2009 |
| JP | 2009-082207 A | 4/2009 |
| JP | 2009-201956 A | 9/2009 |
| JP | 2010-233674 A | 10/2010 |
| KR | 20100064669 A | 6/2010 |
| SU | 1641346 | 4/1991 |
| SU | 1667864 | 8/1991 |
| WO | WO 1993/015701 | 8/1993 |
| WO | WO 1993/017754 | 9/1993 |
| WO | WO 1994/023777 | 10/1994 |
| WO | WO 1995/022612 | 8/1995 |
| WO | WO 1995/033612 | 12/1995 |
| WO | WO 1996/000109 | 4/1996 |
| WO | WO 1996/017648 | 6/1996 |
| WO | WO 1996/037155 | 11/1996 |
| WO | WO 1996/037256 | 11/1996 |
| WO | WO 1997/003629 | 2/1997 |
| WO | WO 1997/003718 | 2/1997 |
| WO | WO 1997/013544 | 4/1997 |
| WO | WO 1997/048440 | 12/1997 |
| WO | WO 1997/048441 | 12/1997 |
| WO | WO 1997/048442 | 12/1997 |
| WO | WO 1998/000193 | 1/1998 |
| WO | WO 1998/028307 | 7/1998 |
| WO | WO 1999/000155 | 1/1999 |
| WO | WO 1999/029298 | 6/1999 |
| WO | WO 1999/029364 | 6/1999 |
| WO | WO 1999/029365 | 6/1999 |
| WO | WO 1999/049874 A1 | 10/1999 |
| WO | WO 1999/061888 | 12/1999 |
| WO | WO 1999/064580 | 12/1999 |
| WO | WO 2000/006166 | 2/2000 |
| WO | WO 2003/026733 A2 | 4/2000 |
| WO | WO 2000/035530 | 6/2000 |
| WO | WO 2000/070406 | 11/2000 |
| WO | WO 2000/074763 A2 | 12/2000 |
| WO | WO 2000/074764 | 12/2000 |
| WO | WO 2000/074765 | 12/2000 |
| WO | WO 2000/074766 | 12/2000 |
| WO | WO 2000/077571 | 12/2000 |
| WO | WO 2001/008242 | 2/2001 |
| WO | WO 2001/036037 | 5/2001 |
| WO | WO 2001/036321 | 5/2001 |
| WO | WO 2001/049362 | 7/2001 |
| WO | WO 2002/002180 | 1/2002 |
| WO | WO 2002/007543 | 1/2002 |
| WO | WO 2002/007813 | 1/2002 |
| WO | WO 2002/017985 | 3/2002 |
| WO | WO 2002/030301 A1 | 4/2002 |
| WO | WO 2002/032331 | 4/2002 |
| WO | WO 2002/032480 | 4/2002 |
| WO | WO 2002/062202 | 8/2002 |
| WO | WO 2002/064193 A2 | 8/2002 |
| WO | WO 2002/072189 | 9/2002 |
| WO | WO 2002/085446 A2 | 10/2002 |
| WO | WO 2002/091922 | 11/2002 |
| WO | WO 2002/100474 | 12/2002 |
| WO | WO 2003/024290 | 3/2003 |
| WO | WO 2003/024518 | 3/2003 |
| WO | WO 2004/000389 A2 | 12/2003 |
| WO | WO 2004/009172 A1 | 1/2004 |
| WO | WO 2004/024224 A1 | 3/2004 |
| WO | WO 2004/030649 A2 | 4/2004 |
| WO | WO 2004/076339 | 9/2004 |
| WO | WO 2004/105729 A2 | 12/2004 |
| WO | WO 2004/110717 | 12/2004 |
| WO | WO 2005/002453 A1 | 1/2005 |
| WO | WO 2005/046769 A2 | 5/2005 |
| WO | WO 2005/065765 A1 | 7/2005 |
| WO | WO 2005/082596 A1 | 9/2005 |
| WO | WO 2005/089857 A1 | 9/2005 |
| WO | WO 2005/094526 | 10/2005 |
| WO | WO 2005/099751 A2 | 10/2005 |
| WO | WO 2005/112984 A2 | 12/2005 |
| WO | WO 2006/020842 | 2/2006 |
| WO | WO 2006/055795 | 5/2006 |
| WO | WO 2006/062848 A1 | 6/2006 |
| WO | WO 2006/086742 A2 | 8/2006 |
| WO | WO 2006/101459 A1 | 9/2006 |
| WO | WO 2007/002521 A2 | 1/2007 |
| WO | WO 2007/002522 A1 | 1/2007 |
| WO | WO 2007/002523 | 1/2007 |
| WO | WO 2007/012114 A1 | 2/2007 |
| WO | WO 2007/030477 A2 | 3/2007 |
| WO | WO 2007/061964 A1 | 5/2007 |
| WO | WO 2007/061972 A2 | 5/2007 |
| WO | WO 2007/075806 A2 | 7/2007 |
| WO | WO 2007/081430 A2 | 7/2007 |
| WO | WO 2007/124411 | 11/2007 |
| WO | WO 2008/011625 | 1/2008 |
| WO | WO 2008/015236 A1 | 2/2008 |
| WO | WO 2008/024141 A2 | 2/2008 |
| WO | WO 2008/091602 | 7/2008 |
| WO | WO 2008/130587 | 10/2008 |
| WO | WO 2008/139648 A1 | 11/2008 |
| WO | WO 2009/039013 A1 | 3/2009 |
| WO | WO 2009/048607 A1 | 4/2009 |
| WO | WO 2009/054988 A1 | 4/2009 |
| WO | WO 2009/142741 A1 | 11/2009 |
| WO | WO 2010/040271 A1 | 4/2010 |
| WO | WO 2010/124255 A2 | 10/2010 |
| WO | WO 2011/121023 A1 | 10/2011 |
| WO | WO 2011/140240 | 10/2011 |
| WO | WO 2011/140274 | 10/2011 |
| WO | WO 2012/054582 A2 | 4/2012 |
| WO | WO 2012/122163 A1 | 9/2012 |
| WO | WO 2012/127249 A1 | 9/2012 |
| WO | WO 2012/153266 A2 | 11/2012 |
| WO | WO 2013/172999 A1 | 11/2013 |
| WO | WO 2014/004301 A1 | 1/2014 |
| WO | WO 2014/077244 A1 | 5/2014 |
| WO | WO 2014/100750 A1 | 6/2014 |
| WO | WO 2014/144973 A1 | 9/2014 |
| WO | WO 2014/150069 A1 | 9/2014 |
| WO | WO 2014/150285 A2 | 9/2014 |
| WO | WO 2014/151654 A1 | 9/2014 |
| WO | WO 2014/164314 A1 | 10/2014 |
| WO | WO 2016/033540 A1 | 3/2016 |
| WO | WO 2016/036866 A1 | 3/2016 |
| WO | WO 2016/073908 A1 | 5/2016 |
| WO | WO 2017/004067 A1 | 1/2017 |

OTHER PUBLICATIONS

Corbett et al., "Skin vaccination against cervical cancer associated human papillomavirus with a novel micro-projection array in a mouse model", PLOS one, vol. 5, No. 10, pp. 1-9 (2010).

Database WPI / Thomson, Accession No. 2014-V89218, Geo et al., "Soluble microneedle patch useful for transderrnal administration of vaccine, comprises water-soluble polymer material as matrix material and soluble microneedle main portion", Application No.

(56) References Cited

OTHER PUBLICATIONS

CN104027324A, Tech Inst Phys. & Chem. Chinese Acad., 3 pages (2014).
Ghosh et al., "Influence of critical parameters of nanosuspension formulation on permeability of a poorly soluble drug through the skin-A case study", vol. 14, No. 3, pp. 1108-1117 (2013).
Guo et al., "Enhanced transcutaneous immunization via dissolving microneedle array loaded with liposome encapsulated antigen and adjuvant", Int. J. Pharm., vol. 447, No. 1-2, pp. 22-30 (2013).
Gupta, "Aluminum compounds as vaccine adjuvants", Adv. Drug Deliv. Rev., vol. 32, No. 3, pp. 155-172 (1998) *Abstract Only*.
Gupta and Rost, "Aluminum compounds as vaccine adjuvants", Vaccine adjuvants: Preparation Methods and Research Protocols, O'Hagan, ed., Humana Press, Inc., Totowa, New Jersey, Meth. Mol. Med., vol. 42, No. 4, No. 4, pp. 65-89 (2000).
International Search Report from International Patent Application No. PCT/US2015/047563 dated Nov. 20. 2015.
International Search Report from International Patent Application No. PCT/US2015/048161 dated Nov. 26, 2015.
Kuroda et al., "Particulate adjuvant and innate immunity: past achievements, present findings, and future prospects", Int. Rev. Immunol., vol. 32, No. 2, pp. 209-220 (2013).
Munks et al., "Aluminum adjuvants elicit fibrin-dependent extracellular traps in vivo", Blood, vol. 116, No. 24, pp. 5191-5199 (2010).
Petrovsky and Aguilar, "Vaccine adjuvants: current state and future trends", Immunol. Cell Biol., vol. 82, No. 5, pp. 488-496 (2004).
Pittman, "Aluminum-containing Vaccine associated adverse events: role of route of administration and gender", Vaccine, vol. 20, pp. s48-s50 (2002).
Prausnitz, "Microneedle-based vaccines", Curr. Top. Microbiol. Immunol., vol. 333, pp. 369-393 (2009).
Sayers et al., "Vaxjo: A Web-Based Vaccine Adjuvant Database and Its Application for Analysis of Vactine Adjuvants and Their Uses in Vaccine Development", J. Biomed. Biotechnol., vol. 2012, Article ID: 831486, 13 pages, doi:10.1155/2012/831486 (2011).
White et al., "Studies on antibody production. III. The alum granuloma", J. Exp. Med, vol. 102, No. 1, pp. 73-82 (1955).
"Eudragt EPO Readymix—Taste masking moisture protection have never been easier" Evonik Industries, Evonik Industries AG, Pharma Polymers & Services, Nov. 2014.
International Search Report from International Patent Application No. PCT/US2014/022836 dated May 9, 2015.
International Search Report from International Patent Application No. PCT/US2014/021841 dated Aug. 11, 2014.
International Search Report from International Patent Application No. PCT/US2014/026179 dated Jul. 18, 2014.
International Search Report from International Patent Application No. PCT/US2014/029601 dated Jul. 1, 2014.
Chun et al., "An array of hollow microcapillaries for the controlled injection of genetic materials into animal/plant cells," IEEE Workshop on Micro Electro Mechanical Systems, pp. 406-411, (1999).
"Extend". Merriam-Webster Online Dictionary, 6 pages. Downloaded on Sep. 7, 2010 from <http://www.merriam-webster.com/dictionary/extend>.
"Extend". Macmillan Online Dictionary, 5 pages, Downloaded on Sep. 7, 2010 from <http://www.macmillandictionary.com/dictionary/american/extend>.
Henry, et al., "Micromachined microneedles for transdermal delivery of drugs", IEEE Workshop on Micro Electro Mechanical Systems, New York, NY, pp. 494-498, (1998).
Henry, et al., "Microfabricated microneedles: A novel approach to transdermal drug delivery", J. Pharmaceutical Science, vol. 87, No. 8, pp. 922-925, (1998).
"Heparin Pregnancy and Breast Feeding Warnings", Drugs.com, Accessed Oct. 8, 2009, <http://www.drugs.com/pregnancy/heparin.html>.
International Search Report from International Patent Application No. PCT/US2000/015612 dated Sep 7, 2000.
International Search Report from International Patent Application No. PCT/US2000/015313 dated Sep. 6, 2000.
International Search Report from International Patent Application No. PCT/US2000/015614 dated Sep. 6, 2000.
International Search Report from International Patent Application No. PCT/US2001/031977 dated Apr. 29, 2002.
International Search Report from International Patent Application No. PCT/US2001/031978 dated Apr. 29, 2002.
International Search Report from International Patent Application No. PCT/US2002/014624 dated Sep. 3, 2002.
International Search Report from International Patent Application No. PCT/US2002/029228 dated Apr. 23, 2003.
International Search Report from International Patent Application No. PCT/US2002/029245 dated Dec. 27, 2002.
International Search Report from International Patent Application No. PCT/US2004/005382 dated Nov. 25, 2004.
International Search Report from International Patent Application No. PCT/US2004/017256 dated May 24, 2005.
International Search Report from International Patent Application No. PCT/US2005/009854 dated Jul. 3, 2008.
International Search Report from International Patent Application No. PCT/US2008/000824 dated Jul. 18, 2008.
International Search Report from International Patent Application No. PCT/US2008/004943 dated Jun. 9, 2009, application now published as International Publication No. WO2008/130587 Oct. 30, 2008.
International Search Report from International Patent Application No. PCT/US2008/011635 dated Dec. 19, 2008, application now published as International Publication No. WO2009/048607 on Apr. 16, 2009.
International Search Report from International Patent Application No. PCT/US2010/032299 dated Dec. 10, 2010, application now published as International Publication No. WO2010/124255 on Oct. 28, 2010.
International Search Report from International Patent Application No. PCT/US2013/077281 dated Mar. 4, 2013.
International Search Report from International Patent Application No. PCT/US2014/022087 dated May 23, 2014.
International Search Report from International Patent Application No. PCT/US2014/022859 dated May 26, 2014.
Matriano, et al., "Macroflux(R) microprojection array patch technology: A new and efficient approach for intracutaneous immunization", Pharm. Res., vol. 19, No. 1, pp. 63-70, (2002).
McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.
Mikszta, et al., "Improved genetic immunization via micromechanical disruption of skin-barrier function and targeted epidermal delivery", Nat. Med., vol. 8, No. 4, pp. 415-419, (2002).
Mikszta, et al., "Protective immunization against inhalation anthrax: A comparison of minimally invasive delivery platforms", J. Inf. Dis., vol. 191, No. 2, pp. 278-288, (2005).
Papautsky, et al., "Micromachined Pipette Arrays," MPA. Proceedings—19th international Conference—IEEE/EMBS, Chicago, IL, USA, pp. 2281-2284 (1997).
Park et al., "Biodegradable polymer microneedles: Febrication, mechanics, and transdermal drug delivery", J. Contr. Rel., vol. 104, pp. 51-66 (2005).
Park, et al. "Polymer Microneedles for Controlled-Release Drug Delivery," Pharmaceutical Research, Kluwer Academic Publishers-Plenum Publishers, NE, vol. 23, No. 5, pp. 1008-1019 (2006).
Prausnitz, et al., "Transdermal transport efficiency during skin electroporation and iontophoresis", J. Contr. Release, vol. 38, pp. 205-217, 1996.
Prausnitz, "Transdermal delivery of macromolecules: Recent advances by modification of skin's barrier properties", ACS Symposium Series No. 675, *Therapeutic Protein and Peptide Formulation and Delivery*, American Chemical Society, Washington DC, Chapter 8, pp. 124-153, (1997).
Rydberg, et al., "Low-molecular-weight heparin preventing and treating DVT", Am. Fam. Physician, vol. 59, No. 6, pp. 1607-1612, (1999).
Sivamani, et al., "Microneedles and transdermal applications", Exp. Opin. Drug Del., vol. 4, No. 1, pp. 19-25, (2007).

(56) References Cited

OTHER PUBLICATIONS

Wouters, et al., "Microelectrochemical systems for drug delivery", Electrochimica Acta., vol. 42, pp. 3385-3390, (1997).
Xia, et al., "Soft Lithography", Angew. Chem. Int. Ed., vol. 37, pp. 551-575, (1998).
Xia, et al., "Soft Lithography" Annu. Rev. Mater. Sci., vol. 28, pp. 153-184 (1998).
International Search Report from International Patent Application No. PCT/US2011/035221 dated Jan. 10, 2012, application now published as International Publication No. WO2011/140240 on Nov. 10, 2011.
International Search Report from International Patent Application No. PCT/US2015/059559 dated Jan. 21, 2016.
International Search Report from International Patent Application No. PCT/US2016/039864 dated Sep. 23, 2016.
Keitel et al., "A randomized clinical trail of acellular pertussis vaccines in healthy adults: Dose-response comparisons of 5 vaccines and implications for booster immunization", J. Infect. Dis., vol. 180, pp. 397-403 (1999).
Lutrol F 68 NF, BASF Pharma Ingredients, accessed from the internet on Sep. 5, 2016 from http://www2.basf.us/Pharma/pdf/Lutrol_F_68.pdf.
Makaida et al., "Poly lactic-co-glycolic acid (PLGA) as biodegradable controlled drug delivery carrier", Polymers (Basel), vol. 3, No. 3, pp. 1377-1397 (2011).
Vitiello et al., "Development of a lipopeptide-based therapeutic vaccine to treat chronic HBV infection", J. Clin. Invest., vol. 95, pp. 341-349 (1995).
Julinova et al., "Initiating biodegradation of polyvinylpyrrolidone in aqueous aerobic environment", Proceedings of ECOpole, vol. 6, No. 1, pp. 121-127 (2012).
Kunduru et al., "Biodegradable polymers: Medical Applications", Encyclopedia of Polymer Science and Technology, pp. 1-22 (2016) DOI: 10.1002/0471440264.pst027.pub2.

\* cited by examiner

MICROPROJECTION APPLICATORS AND METHODS OF USE

CROSS-REFERENCE TO RELATED APPLICATIONS

This application claims the benefit of U.S. Provisional Application No. 61/778,274, filed Mar. 12, 2013, which is incorporated herein by reference in its entirety.

TECHNICAL FIELD

The subject matter described herein relates generally to a method and delivery system for drug delivery using microprojections, and more specifically to applicators for applying an array of microprojections.

BACKGROUND

Arrays of microneedles were proposed as a way of administering drugs through the skin in the 1970s, for example in U.S. Pat. No. 3,964,482. Microneedle or microstructure arrays can facilitate the passage of drugs through or into human skin and other biological membranes in circumstances where ordinary transdermal administration is inadequate. Microstructure arrays can also be used to sample fluids found in the vicinity of a biological membrane such as interstitial fluid, which is then tested for the presence of biomarkers.

In recent years it has become more feasible to manufacture microstructure arrays in a way that makes their widespread use financially feasible. U.S. Pat. No. 6,451,240 discloses some methods of manufacturing microneedle arrays. If the arrays are sufficiently inexpensive, for example, they may be marketed as disposable devices. A disposable device may be preferable to a reusable one in order to avoid the question of the integrity of the device being compromised by previous use and to avoid the potential need of resterilizing the device after each use and maintaining it in controlled storage.

In addition to cost, integrity and sterility, a further issue with microneedle arrays is bioavailability of the active agent. An intravenous injection delivers a precise quantity of an active agent to the circulation. A subcutaneous or intramuscular injection delivers a precise quantity of an active agent into the tissue, but the quantity of active agent delivered to the circulation and the rate at which active ingredient is delivered are affected by the type of surrounding tissue, circulation, and possibly other factors. When a drug is delivered orally, the resulting blood levels may exhibit substantial variation among patients due to metabolism and other factors, but minimal therapeutic levels can be assured for most patients, for example, because the rate of metabolism has an upper limit and because there is long experience with the absorption of many drugs from oral formulations. When a drug is delivered to unmodified skin by a conventional transdermal patch, the bypassing of the hepatic circulation may lessen the effect of liver metabolism on bioavailability. On the other hand, with a conventional transdermal patch, differences in skin permeability are an additional factor leading to differences in bioavailability.

Microneedles manipulate the permeability of the skin with respect to the active agent. Variability in the permeability enhancement created by different applications of the microneedles will result in variations in the rate of transfer through the skin, the amount transferred through the skin and the bioavailability. Variability of skin permeability enhancement on the application of a microneedle array can result from application on different patients. Particular concern exists, of course, if the enhancement is small in particular patient populations so that the administration of the drug will not produce a therapeutically effective dosing (e.g., adequate blood levels) in those populations. Concern may arise also if the enhancement is sometimes undesirably small in a patient, even if at other times the enhancement is as expected in that patient, depending on details of how and where the microneedle array is applied.

A typical microneedle array comprises microneedles projecting from a base of a particular thickness, which may be of any shape, for example square, rectangular, triangular, or circular. The microneedles themselves may have a variety of shapes. While an array could be pressed by hand into skin, it has also been proposed to use a variety of devices to hold the microneedle array as it is being applied or to facilitate in one way or another the process of microneedle array application to the skin or other biological membrane. Such devices may broadly be referred to as "applicators." Applicators may for example reduce the variations in force, velocity, and skin tension that occur when a microneedle array is pressed by hand into the skin. Variations in force, velocity, and skin tension can result in variations in permeability enhancement.

In some applications of microneedle arrays, they may be applied to the skin or other biological membrane in order to form microchannels and then are more or less immediately withdrawn. In other applications the microneedle array may be held in place for a longer period of time. The design of the applicator may naturally be influenced by how long the microneedles are expected to stay in place.

Applicators for microneedles comprising components which have two stable states have been described in U.S. Published Patent Application No. 2008/0183144. The existence of two stable states is a feature generally desired in an applicator because the energy difference between the two stable states can allow each use of the applicator to employ a fixed amount of energy in order to cause penetration, improving reproducibility.

In some other prior art applicator designs, the energy storage element, such as a spring or elastic element, may exert forces on one or more components of the applicators, leading to dimensional distortion and creep over an extended period of time. These effects are undesirable as they lead to variations in the applicator geometry and a loss in the stored elastic energy over time. Therefore, there is a need for an applicator which has energy storage elements that do not exert forces on one or more components of the applicator and/or has elements that reduces or eliminates the stress being applied to components of the applicator to eliminate or reduce dimensional distortion and creep.

In some other prior art applicator designs, a plunger is released at one or more points by pushing several projections away from contact with the plunger. The release may not be simultaneous resulting in tilting of the plunger during release which results in poor penetration of the microstructure array (MSA) into skin. Therefore, there is a need for an applicator that releases the plunger without adversely affecting the trajectory of the plunger.

In the use of microneedle arrays, particularly when the arrays are kept in place for a prolonged period of time, devices to transport the drug substance to the skin may be employed. A very simple such device may, for example, comprise a reservoir for liquid or solid drug substance which is kept in contact with the base, with the liquid drug substance flowing through small apertures in the base or by diffusion when solid drug substance is used. Another device suitable for delivering the drug substance to skin is described in U.S. Published Patent Application No. 2005/0094526. Rotary applicators have been disclosed in U.S. Published Patent Application No. 2004/0087992. There is some disclosure relating to applicators, for example, in U.S. Pat. Nos. 6,537,242, 6,743,211 and 7,087,035.

There is a need in the art for applicators and related devices suitable for use with microneedle arrays, for example, in order to assist in making the process of drug delivery more user friendly and uniform across patients and for different applications to the same patient.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, an applicator comprising a plate member, a blocking element, a plunger, an energy-storing element, and an actuating member is provided. In an embodiment, the plate member is a rigid plate member having an upper surface and a lower surface. In a further embodiment, the plate member includes at least one opening. The blocking element is in contact with the upper surface of the plate member and is capable of moving between a first position and a second position in an embodiment. In another embodiment, the plunger has a proximal end, a distal end and a shaft extending therebetween. The proximal end of the shaft may be at least partially retained by the blocking member in its first position. In an embodiment, the energy-storing element is positioned between the lower surface of the plate member and the distal end of the plunger. In a further embodiment, the actuating member has an external surface for application of a force and at least one surface in mechanical communication with the blocking element when the blocking element is in the first position. In another embodiment, the actuating member moves the blocking element from the first position to the second position when a force is applied to the external surface of the actuating member. The energy-storing element is released as the blocking element is moved from its first position to its second position.

In an aspect, the applicator further comprises at least one microprojection positioned on a bottom surface of the plunger distal end. In another embodiment, the at least one microprojection is a microprojection array, a hypodermic needle or a trocar. In a further embodiment, the microprojection array comprises a plurality of dissolvable or erodible microprojections. In other embodiments, at least a portion of the plurality of microprojections is detachable from the microprojection array. In yet another embodiment, the at least one microprojection includes at least one therapeutic agent.

In an embodiment, the applicator further comprises at least one flexure element in mechanical communication with the blocking element. In another embodiment, the flexure element directs the blocking element into the plunger in the blocking element first position.

In an embodiment, the actuating member causes the blocking element to have a linear displacement. In another embodiment, the actuating member causes the blocking element to have a rotational displacement.

In an embodiment, the energy-storing element is an elastic energy element. In another embodiment, the elastic energy element is selected from a compression spring, a coil spring, or a wave spring.

In an embodiment, the plunger proximal end is dimensioned to be retained by the blocking element in its first position. In a further embodiment, the plunger proximal end is retained by the blocking element in its first position by a ledge at least partially circumscribing the plunger shaft.

In an embodiment, the plunger shaft has a length and the energy-storing element is selected to provide a force on the plunger that causes the plunger to travel a distance longer than the length of the shaft.

In an embodiment, the at least one opening of the plate has a shape selected from circular, oval, rectangular, and square.

In an embodiment, the applicator further comprises a housing member. In another embodiment, the housing member includes an opening through which an external surface of the actuating member can be accessed. In a further embodiment, the housing opening is sized to receive at least a part of the external surface of the actuating member. In another embodiment, the housing includes a surface on which an adhesive is or can be applied, to secure the housing to a subject. In a further embodiment, the adhesive layer at least partially surrounds the at least one microprojection. In yet another embodiment, the length of the plunger shaft is such that it extends beyond the surface on which the adhesive is or can be applied.

In an embodiment, the applicator further comprises comprising a backing member positioned on a distal surface of the plunger distal end, wherein the backing member comprises the at least one microprojection. In a further embodiment, the backing member is detachable from the plunger distal end. In another embodiment, the backing member comprises a support layer adjacent the distal surface of the plunger distal end and an adhesive layer, wherein the at least one microprojection is positioned distal to the adhesive layer. In yet another embodiment, the at least one microprojection is a microprojection array positioned distal to the adhesive layer.

In embodiments, at least the plate and the plunger are formed from a material with an elastic modulus between about 0.5 to 500 KSI. In other embodiments, at least the plate and the plunger are formed from a metal. In a further embodiment, at least the blocking element is formed from a material with an elastic modulus between about 0.5 to 500 KSI. In yet another embodiment, the blocking element is formed from a metal. In embodiments, the metal is selected from stainless steel, carbon steel, titanium, and alloys thereof.

In an embodiment, the applicator further comprises a damper positioned between the energy-storing element and a proximal surface of the plunger distal end.

In a further aspect, a method for delivering at least one therapeutic agent to a subject is contemplated. In an embodiment, the method comprises applying a microprojection array included on a distal end of an applicator plunger to a subject's skin site; contacting an external surface of the applicator actuating member to actuate the actuator from a first position to a second position where the actuator is in mechanical communication with a blocking element; moving the blocking element from a first position in contact with a proximal end of the plunger to a second position; releasing the plunger from a first position in contact with the blocking member to a second position; releasing an energy-storing element to deploy the plunger into contact with a subject's skin; and delivering the at least one therapeutic agent from the microprojection array to the subject. In another embodiment, the method further comprises adhering the applicator to the subject's skin. In a further embodiment, moving the blocking element effects movement of the plunger from a retracted position to a deployed position. In another embodiment, contacting the external surface of the actuating member effects movement of the plunger from a retracted position to a deployed position. In a further embodiment, the plunger in the deployed position has an equilibrium position such that the distal end of the plunger on which the microprojection array is affixed is positioned below a surface of the skin. In yet another embodiment, the equilibrium position is about 0.03-0.2 inches below the surface of the skin of the subject. In another embodiment, the method further comprises detaching a backing member such that the backing member and the microprotrusion array are retained on the subject's skin.

In another aspect, an applicator comprising a planar plate having an upper surface and a lower surface and at least one opening; a planar flexure element in contact with the upper surface of the plate member, the flexure element (i) having a gap capable of moving between first and second positions and (ii) being positioned to align the gap with the opening in the plate member; a plunger slidably disposed within the aligned gap and opening; an energy-storing element positioned between the lower surface of the plate member and the distal end of the plunger; and an actuating member. In an embodiment, the plunger has a shaft with a distal end on which at least one microstructure can be retained. In a further embodiment, the plunger has a proximal end dimensioned such that the proximal end is retained by the gap when the gap is in its first position and the proximal end passes through the gap in its second position. In other embodiments, the actuating member has an external surface and a polyhedral-shaped member. In yet another embodiment, the polyhedral-shaped member is dimensioned to move the gap between its first and second positions when the external surface of the actuating member is contacted with sufficient force to effect release of the energy storing element. In further embodiments, the polyhedral-shaped member comprises between 2-8 faces. In even further embodiments, the polyhedral-shaped member has a gap dimensioned to receive the proximal end of the plunger.

In an embodiment, the energy-storing element is an elastic energy element. In other embodiments, the elastic energy element is selected from a compression spring, a coil spring, and a wave spring.

In an embodiment, the proximal end of the plunger is dimensioned to be retained by the gap in its first position by a ledge at least partially circumscribing the plunger shaft.

In an embodiment, the plate member opening has a shape selected from circular, oval, rectangular, and square. In another embodiment, the opening is centrally located on the plate.

In an embodiment, at least the flexure element and the plunger are formed from a material having an elastic modulus between about 0.5 to 500 KSI. In other embodiments, the material is a metal. In further embodiments, the metal is selected from stainless steel, carbon steel, titanium, and alloys thereof.

In embodiments, the applicator further comprises a housing member with an opening through which the external surface of the actuating member can be received. In other embodiments, the housing includes a surface on which an adhesive is or can be applied to secure the housing to a subject.

In embodiments, the plunger shaft has a length and the energy-storing element is selected to provide a force on the plunger that causes the plunger to travel a distance longer than the length of the shaft. In further embodiments, the length of the plunger shaft is such that it extends beyond the surface on which the adhesive is or can be applied.

In embodiments, the at least one microprojection is a microprojection array, a hypodermic needle or a trocar. In additional embodiments, the microprojection array comprises a plurality of dissolvable or erodible microprojections. In further embodiments, the plurality of microprojections includes a therapeutic agent. In even further embodiments, at least a portion of the plurality of microprojections is detachable from the microprojection array. In yet further embodiments, the applicator further comprises a backing member positioned on a bottom surface of the plunger distal end, wherein the backing member comprises the at least one microprojection. In other embodiments, the backing member is detachable from the plunger distal end. In additional embodiments, the backing layer comprises a support layer adjacent a distal surface of the plunger distal end and an adhesive layer, wherein the at least one microprojection is positioned distal to the adhesive layer. In further embodiments, the at least one microprojection is a microprojection array positioned distal to the adhesive layer. In even further embodiments, the adhesive at least partially surrounds the at least one microprojection.

In embodiments, the applicator further includes a damper positioned between the energy-storing element and a proximal surface of the plunger distal end.

In yet another aspect, a method for delivering a therapeutic agent is contemplated. In an embodiment, the method comprises applying a microprojection array affixed to an applicator; contacting the external surface of the actuating member to actuate the actuator from a first position to a second position, whereby a gap is moved from the first position to the second position; releasing the plunger from a restrained position to a deployed position in contact with the subject's skin; and delivering the therapeutic agent from the microprojection array to the subject. In an embodiment, the microprojection array is affixed to the distal end of a plunger. In embodiments, the method further comprises adhering the applicator to the subject's, skin. In additional embodiments, the microprojection array comprises a plurality of microprojections, and in the deployed position, the plunger has an equilibrium position such that the distal end of the plunger on which at least a portion of the plurality of microprojections are positioned below the surface of the skin. In further embodiments, the equilibrium position is about 0.03-0.2 inches below the surface of the skin of the subject.

In an embodiment, deploying the plunger further comprises detaching the backing member such that the backing member and the microprotrusion array are retained on the subject's skin.

Additional embodiments of the present devices, apparatuses, methods, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present devices, apparatuses, and methods are set forth in the following description and claims, particularly when considered in conjunction with the accompanying examples and drawings.

Figure 1A:
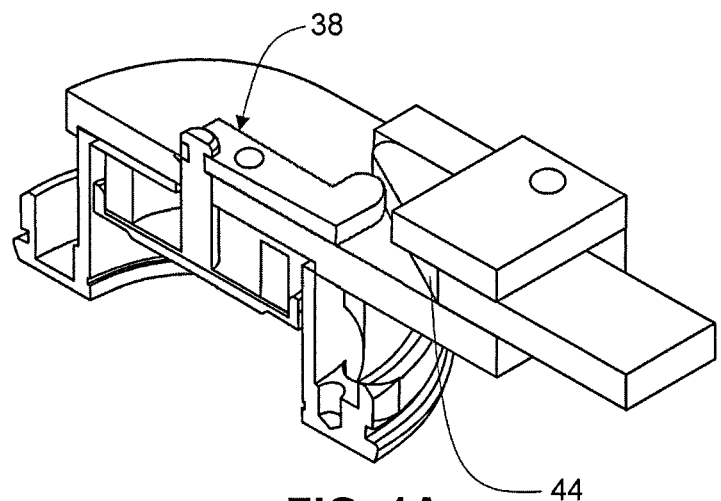
FIGS. 1A-1B are illustrations of top perspective views of an exemplary applicator device showing select features.

It will be appreciated that the thicknesses and shapes for the various applicators and microstructure arrays have been exaggerated in the drawings to facilitate understanding of the device. The drawings are not necessarily "to scale,"

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

I. Definitions

As used in this specification, the singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

In describing and claiming the present invention, the following terminology will be used in accordance with the definitions described below.

In discussing the applicators and arrays, the term "downward" is sometimes used to describe the direction in which microprotrusions are pressed into skin and "upward to describe the opposite direction. However, those of skill in the art will understand that the applicators can be used where the microprotrusions are pressed into skin at an angle to the direction of the earth's gravity, or even in a direction contrary to that of the earth's gravity. In many applicators described herein, the energy for pressing the microprotrusions is provided primarily by an energy-storage member and so efficiency is not much affected by the orientation of the skin relative to the earth's gravity.

The terms "microprotrusion", "microprojection", "microstructure" or "microneedle" are used interchangeably herein to refer to elements adapted to penetrate or pierce at least a portion of the stratum corneum or other biological membranes. For example, illustrative microstructures may include, in addition to those provided herein, microblades as described in U.S. Pat. No. 6,219,574, edged microneedles as described in U.S. Pat. No. 6,652,478, and microprotrusions as described in U.S. Patent Publication No. U.S. 2008/0269685.

The term "microprotrusion array" for purposes herein is intended to denote a two-dimensional or a three-dimensional arrangement of microprotrusions, microprojections, or microneedles. The arrangement may be regular according to a repeating geometric pattern or it may be irregular.

"Optional" or "optionally" means that the subsequently described circumstance may or may not occur, so that the description includes instances where the circumstance occurs and instances where it does not.

"Substantially" or "essentially" means nearly totally or completely, for instance, 80-85%, 80-90%, 80-95%, 85-90%, 85-95%, 90-95% or greater of some given quantity.

In this application reference is often made for convenience to "skin" as the biological membrane which the microneedles penetrate. It will be understood by persons of skill in the art that in most or all instances the same inventive principles apply to the use of microneedles to penetrate other biological membranes such as, for example, those which line the interior of the mouth or biological membranes which are exposed during surgery. In other embodiments, the inventive principles may apply to the use of microneedles for cell walls. For example, the microneedles described herein may be used to treat a condition of the skin where certain cells that present on the surface are targeted by the microneedles.

"Transdermal" refers to the delivery of an agent into and/or through the skin or for local and/or systemic therapy. The same inventive principles apply to administration through other biological membranes such as those which line the interior of the mouth, gastro-intestinal tract, blood-brain barrier, or other body tissues or organs or biological membranes which are exposed or accessible during surgery or during procedures such as laparoscopy or endoscopy.

II. Microstructure Applicators

Before describing the present subject matter in detail, it is to be understood that this invention is not limited to specific materials or device structures, as such may vary. It is also to be understood that the terminology used herein is for the purpose of describing particular embodiments only, and is not intended to be limiting.

A. Blocking Element Release Applicator

In one aspect, an applicator for delivery of a needle, microneedle, microprojection, microstructure, or arrays thereof is described herein. The applicator comprises an actuator or actuating member, a blocking element or member, a plunger or piston, a plate or holder having at least one opening, and an energy-storing element. The applicator operates by applying a force to the actuating member above a threshold to release the plunger which is retained by the blocking member or element.

The applicator 10 includes a planar plate member or holder 12 having an upper or proximal surface 34 and a lower, under, or distal surface 36. The plate member has at least one opening 22 extending through the plate. The plate member may be flexible, rigid or substantially rigid. Preferably, the plate member has sufficient mechanical strength and/or is sufficiently rigid to constrain, along with a plunger distal end 28, an energy storage element 20 as describe more fully below. The at least one opening is dimensioned to allow at least a portion of a plunger or piston 16 to pass therethrough. In one embodiment, the at least one opening has a suitable dimension for the plunger to be slidably accommodated therein. A blocking or retaining element 14 is positioned adjacent the proximal surface of the plate at or near the at least one opening. The blocking element is capable of moving from a first position 38 as shown in FIG. 1A in which the plunger is retained by the blocking element to a second position 40 seen in FIG. 1B in which the plunger is released. The blocking element may be retained by or secured to the plate by any suitable manner including, but not limited to, a mechanical feature such as a locking system, one or more fasteners, and/or an adhesive.

The applicator further includes a plunger, piston or other elongate structure 16 having a central post or shaft 26 with a proximal end or portion 24 and a distal end or portion 28. The shaft preferably extends at least partially between the proximal and distal ends or portions. The proximal end of the plunger is preferably sized and shaped so that it is at least partially slidably positionable through the at least one opening in the plate. It will be appreciated that the plunger may have any suitable shape or size. As shown at least in FIGS. 1B and 2, one suitable shape comprises a cylindrical shaft with a circular or cylindrical proximal end. In this particular embodiment, the distal end has a circular plate shape. It will be appreciated, however, that other shapes are suitable including, but not limited to a rectangular prism or other polygonal prisms. It will further be appreciated that the shaft, proximal end, and distal end may each have a different geometry. As one example, the shaft and proximal end may be cylindrical with the distal end having a square or rectangular shape. It will further be appreciated that one or both of the proximal and distal ends may be a plate having a circular, square, rectangular, elliptical or irregular shape. In one embodiment, the proximal end has a wider diameter than a diameter of the central shaft. The plunger is at least partially slidably disposed within the at least one plate opening such that the proximal end of the plunger may pass at least partially through the opening. In one embodiment, the proximal end of the plunger includes plunger retaining area 32 that is typically an opening, cut-out, edge, ledge or undercut that is dimensioned to receive at least a portion of the blocking element. In the embodiment shown in FIG. 1A, the plunger proximal portion includes a cut-out portion for receiving at least a portion of the blocking element when the element is in the first position. In this embodiment, at least the proximal end of the plunger rests on and is retained by a portion of the blocking element. The plunger proximal end is held in a restrained or constrained position. In the second position, the blocking element is removed from the cut-out portion of the plunger proximal portion. The plunger proximal end is then free to slide through the at least one opening toward a patient's skin. In one embodiment, the proximal end of the plunger is dimensioned to be retained by the at least one opening in its first position by a ledge at least partially circumscribing the plunger shaft. Thus, at least a portion of the ledge, underside or the undercut of the proximal end of the plunger rests on an upper or proximal surface of the blocking element. Preferably, the plunger proximal end is at least partially surrounded by the blocking member such that the proximal end is supported and retained by or on the proximal surface of the blocking member partially or substantially around at least the edge of the proximal end of the plunger. The proximal end of the plunger may have any suitable size and shape.

Figure 1B:
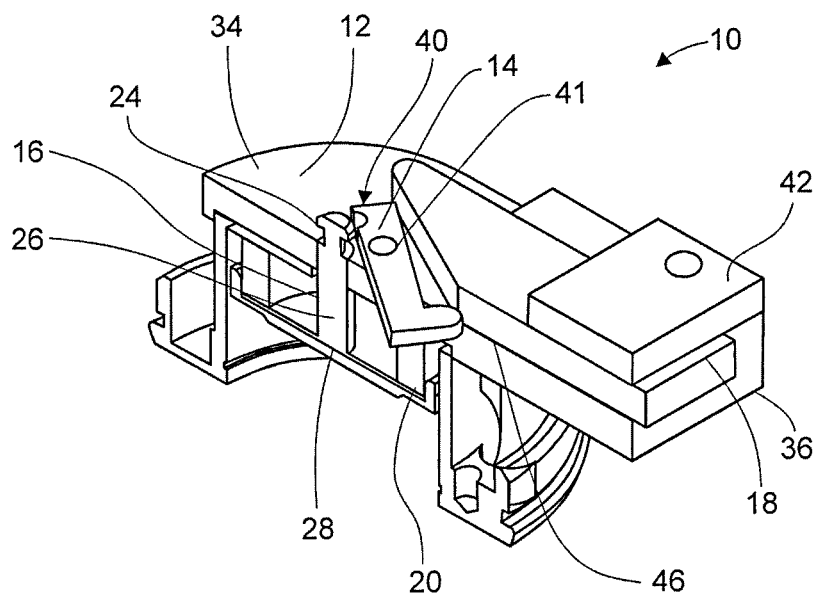

FIGS. 1A-1B show one exemplary configuration for moving the blocking element from a first position to a second position. As seen in FIG. 1A, a portion of the blocking member fits into a cutout or plunger retaining area 32 in the proximal portion of the plunger. An actuator or actuating member or element 18 is used to contact the blocking member and move the blocking member from its first position to its second position. The actuating member 18 is typically positioned adjacent the proximal surface of the plate at or near at least one end of the blocking member. The actuating member is capable of moving from a first position 44 as shown in FIG. 1A to a second position 46 in which the actuating member contacts and moves the blocking member to its second position 40 as shown in FIG. 1B. The actuating member may be retained by or secured to the plate by any suitable manner including, but not limited to, a mechanical feature such as a locking system, one or more fasteners, and/or an adhesive. In one exemplary embodiment the actuating member is secured to the plate by an actuator holder or retainer 42 as shown in FIGS. 1A-1B.

Figure 2:
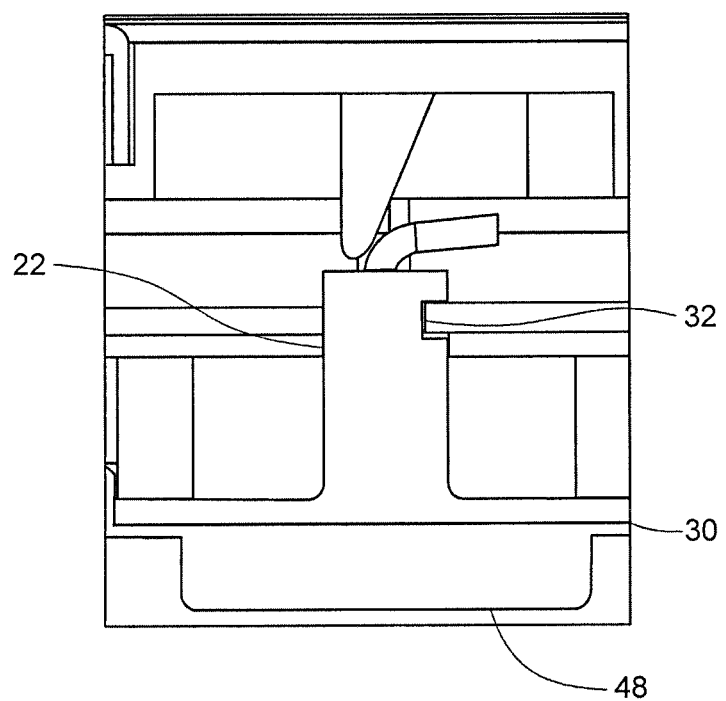
FIG. 2 is an illustration of a side view of an exemplary applicator device.

As the actuator is moved from the first position 44 (FIG. 1A) to the second position 46 (FIG. 1B), the actuator contacts the blocking element and moves the blocking element from its first position 38 to its second position 40 and thereby releasing the plunger. In the exemplary embodiment shown, the blocking element pivots around a central retaining point 41 from the first position to the second position. The blocking element may be any suitable shape and size. In an exemplary embodiment, the blocking element includes a protrusion for contact by the actuating member. In the embodiment of FIGS. 1A-1B, the blocking member is L-shaped. In other embodiments, the blocking member is polygonal or irregular shaped. As the actuating member moves from its first position to its second position, the actuating member contacts the blocking member protrusion and pivotally moves the blocking member. As the blocking member pivots around a pivot point 41, the portion of the blocking member retaining the plunger moves away from the plunger retaining area 32, thereby releasing the plunger. In an embodiment, the actuating member has a polygonal shape. In embodiments, the actuating member has a wedge shape having a wide base and tapering to a narrower tip. In the embodiment of FIG. 1A, the area of the actuating member that contacts the blocking member has a sloped shape. Therefore, as the actuation member is moved, a progressively wider portion of the actuation member contacts the blocking member protrusion. In another embodiment as shown in FIG. 2, the actuating member moves in a downward direction to contact and move the blocking member from contact with the plunger retaining area 32. It will be appreciated that the blocking member and actuating member may each have any shape that is suitable to allow the actuating member to push, move, or rotate the blocking member away from or out of engagement with the plunger proximal end. In embodiments, the actuation member causes the blocking element to have a linear or rotational displacement. In embodiments, the plunger and blocking element are placed close to the central axis (or rotational axis) of the plunger.

Pressure may be applied to move the actuating member 18 from its first position 44 to its second position 46 by any suitable means including manual or mechanical. Where the pressure is manually applied, the actuating member has an external surface that is suitable for contact by a user or otherwise includes structure that allows a user to apply the appropriate pressure to the actuating member. In non-limiting embodiments, a force of about 0.5-10 lb is applied to the actuating member.

The force needed to actuate the device is that required to move the actuating member from a first position to a second position and therefore move the blocking member from a first position to a second position. This force depends on their precise dimensions and the material characteristics (e.g., Young's modulus) of the material out of which they are made. In other embodiments, the force depends on the coefficient of friction, contact force, and/or mechanical advantage. The coefficient of friction may be modified by using finishes and/or coatings. The contact force depends on the spring constant and the energy stored in the energy storing element. Mechanical advantage depends on the design elements and their precise dimensions.

The bottom surface 30 of the plunger 16 further includes at least one needle, a microprojection array, a passive transdermal patch, or other delivery device for transdermal administration of one or more therapeutic agents. In an exemplary embodiment, a microprojection array 48 is affixed, attached, adhered to, or integral with the bottom surface 48 of the plunger. In one embodiment, the delivery device is removably attached to the plunger distal surface. General features for microprojection arrays are described, for example, in U.S. Publication Nos. 2008/0269685, 2011/0276028, and U.S. Pat. Nos. 7,416,541, 7,578,954, 7,108,681, each of which are incorporated herein by reference. In embodiments, the microprojection is a hypodermic needle or a trocar. In further embodiments, the microprojection array comprises a plurality of microprojections, at least some of which are dissolvable or erodible microprojections. In further embodiments, at least some of the microprojections include at least one therapeutic agent. Further, at least a portion of the microprojections may be detachable from the microprojection array. Detachable microprojection arrays are described in U.S. patent application Ser. No. 61/745,513, which is incorporated herein by reference.

In one non-limiting embodiment the microprojection array or other delivery device is affixed or attached to the plunger distal end using an adhesive. Suitable adhesives include, but are not limited to, acrylic adhesives, acrylate adhesives, pressure sensitive adhesives, double-sided adhesive tape, double sided adhesive coated nonwoven or porous film, and UV curable adhesives. It will be appreciated that any medical device adhesive known in the art would be suitable. In another embodiment, at least a portion of the microstructure array or other delivery device is integral with at least a portion of the plunger distal end.

The sizes of the microneedles and other protrusions for use with this invention will be a function of the manufacturing technology and of the precise application. In general, however, microneedles and other microprotrusions used in practice may be expected to have a length of about 20 to about 1000 microns, more preferably from about 50 to about 750 microns and most preferably from about 100 to about 500 microns. Often it will be desired that the microprotrusions will be long enough to penetrate at least partially through the stratum corneum layer of skin at some suitable point of application on the human body, for example the thigh, hip, arm, or torso.

The plate member, plunger, and blocking member may be formed of any suitable material. In one non-limiting embodiment, the plate member and plunger are at least partially formed of a material having an elastic modulus of between about 0.5-500 KSI. In an embodiment, at least one of the plate member or the plunger is formed of a metal including, but not limited to stainless steel, carbon steel, titanium, and alloys thereof. In one preferred embodiment at least the plate member and the plunger are formed of a metal.

The applicator further includes at least one energy-storing element 20 positioned at least partially between a lower surface of the plate member and the distal end of the plunger. Preferably, the energy storing element(s) are retained and/or supported between the plate and the plunger distal end.

Any suitable energy storing element is contemplated including, but not limited to springs or elastic components. In non-limiting embodiments, the energy storing element is an elastic storage element, a compression spring, a coil spring, or a wave spring device. When the plunger is retained by the blocking member, the energy-storage member is restrained in a high energy position of stored energy, and when the plunger is released from the blocking member, the energy-storage member releases its stored energy and in so doing moves the plunger. The energy storing element is typically maintained in a constrained or restrained position between the proximal surface of the plunger and the distal surface of the plate member when the plunger proximal end is retained by the blocking member. When the plunger proximal end is released from the blocking member, the energy storing element is released from the constrained position and the stored energy pushes the plunger distal end away from the plate and toward the patient's skin. The amount of energy stored by the energy storing element may be adjusted based on the application area and/or microstructure structural features. The amount of stored energy may be, for example, in the range of about 0.1 J to about 10 J, or in the range of about 0.25 J to about 1 J. In an embodiment, the energy storing member is selected to provide a force on the plunger sufficient to cause the plunger to travel a distance longer than the length of the plunger shaft. In other embodiments including a housing discussed below, the energy storing member is selected to provide a force on the plunger sufficient to cause the plunger to travel a sufficient distance so that at least a portion of the plunger distal end exits the housing distal end.

A skilled artisan will appreciate the wide variety of energy-storage members that would be suitable for use, and some examples are illustrated in U.S. Patent Publication No. 2011/0276027, which is incorporated herein by reference in its entirety. It is to be understood that other similar shapes, including but not limited to other axisymmetric shapes, may be used to create an energy-storage member. Further, nonsymmetric shapes may be used to create an energy-storage member. It is also to be understood that the energy-storage member may comprise a plurality of individual energy-storage members that may or may not be identical in size, shape, and material. The use of a plurality of individual energy-storage members may be useful to allow alteration of plunger velocity, energy, activation force, or other performance characteristics in ways that may not be achievable or different than with a single energy-storage member.

The material from which the energy storage member is manufactured is variable, and a skilled artisan will appreciate that it is selected based on the several design considerations, including storage life and desired application force, which of course will also depend on the configuration of the member. Exemplary materials include metals, alloys, plastics, and specific examples include stainless steel and thermoplastics.

The velocity of the microprojection array or other delivery device at the time of contact with skin may be adjusted, for example, by varying the amount of stored energy in the energy-storing element and/or by changing the mass of the plunger. This is done, for example, by controlling the energy-storing element's geometric design and the properties of the material(s) out of which the energy-storing element is made. The energy-storing element may have a compressed form in which the degree of compression (e.g., in one spatial direction) controls the amount of energy stored.

When the energy storing element is stored in compressed form, a variety of mechanisms external to the element, but forming part of the applicator, may be employed to release the compression and allow the element to uncompress and therefore release some or all of its energy.

The velocity of the microprojection array or other delivery device at the time of contact with the skin may lie, for example, within the range of 0.1 m/s to 20 m/s, or within the range of 0.5 m/s to 10 m/s. In general, the stored energy may be employed in moving the microprojection array or other delivery device into contact with the skin as well as in overcoming any forces (e.g., from other components of the applicator) acting on the microprojection array or other delivery device. In addition, the stored energy may be employed in moving other components which, in accordance with the design of the applicator, must also move as the microprojection array or other delivery device moves towards the skin.

Figure 3:
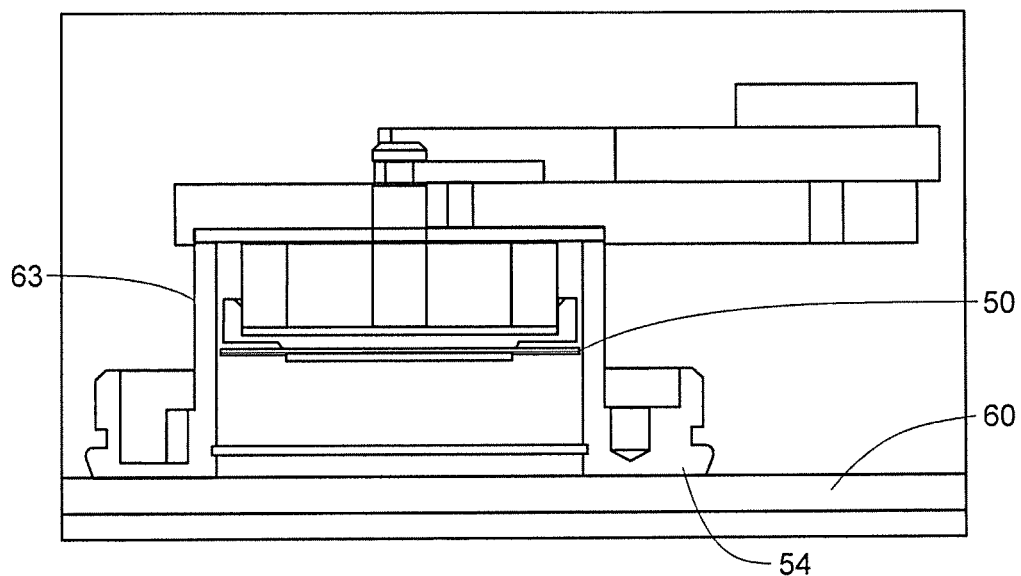
FIG. 3 is an illustration of a side view of an exemplary applicator device.
Figure 10:
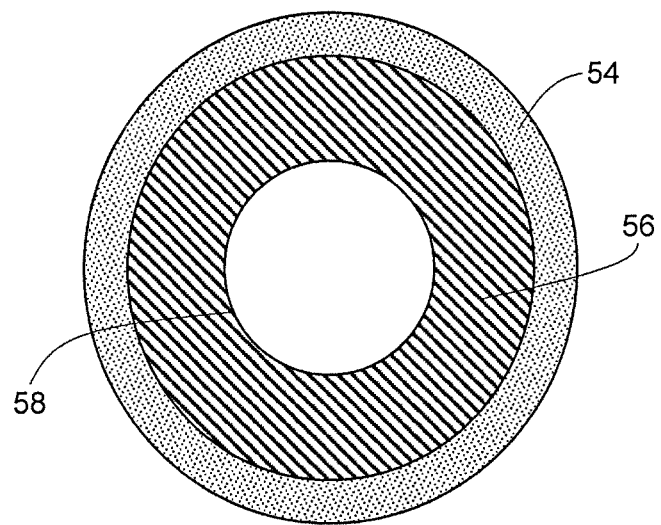
FIG. 10 is an illustration of a bottom view of an exemplary housing for the device.

The applicator may further include an outer housing 63 at least partially surrounding or enclosing applicator. In the embodiment shown in FIG. 3, at least a portion of the plunger in the retained or constrained position and the energy-storing element(s) are enclosed by the housing. Preferably at least part of the actuating member is accessible from the housing so that the user can apply pressure to the actuating member. It will be appreciated that at least a portion of the plunger extends beyond a distal end of the housing when released from the blocking member and/or at equilibrium so that the microprojection array or other delivery device is able to contact skin. It will also be appreciated that only a portion of the microstructures themselves need to extend beyond the housing distal end in order to penetrate skin. As seen in FIG. 3, the distal end of the housing may include a skin contacting area or member 54 that is placed against a subject or patient's skin 60. The skin contacting area 54 may be an annular ring positioned around an opening 58 for the microprojection array or other delivery device as shown in FIG. 10. The skin contacting area may further include an adhesive 56 for adhering the housing to the skin. The adhesive may be applied at least partially on the annular skin contacting area. In embodiments, the housing includes a surface on which an adhesive is or can be applied to secure the housing to a second surface. It will be appreciated that the skin contacting area may surround all or a part of an opening 58 for the microstructure array or other delivery device attached to the plunger distal end to pass through.

Applicators contemplated herein will commonly have at least two states or configurations. In the first state or configuration, the proximal end of the plunger is retained by the plate member. In the first state or configuration, the energy storing element is restrained between the plate element and the plunger distal end in a high energy position. This is typically expected to be the state of the applicator following manufacturing and during shipping and storage. When the plunger proximal end passes through the at least one opening, the energy storing element is released from the constrained state and releases all or a part of the stored energy. In this second state or configuration, which is arrived at by operating the actuating member or element, the microprojection array or other delivery device projects outward from the applicator.

The materials from which the applicator components are manufactured can be selected from a wide variety known to a skilled artisan. For example, a filled polymer material is suitable for manufacture of at least the outer cover or housing, the blocking member and/or the actuating member. A skilled artisan will understand the various material properties to be considered when selecting a suitable material for each component part.

B. Opening Release Applicator

In another aspect, an applicator for delivery of a needle, microneedle, microprojection, microstructure, arrays thereof, or other delivery device is described herein. The applicator comprises an actuator or actuating member, a plunger or piston, a plate or holder having an opening, and an energy-storing element. The applicator operates by applying a force to the actuating member above a threshold to release the plunger which is retained by the opening of the plate or a flexure element.

Figure 7:
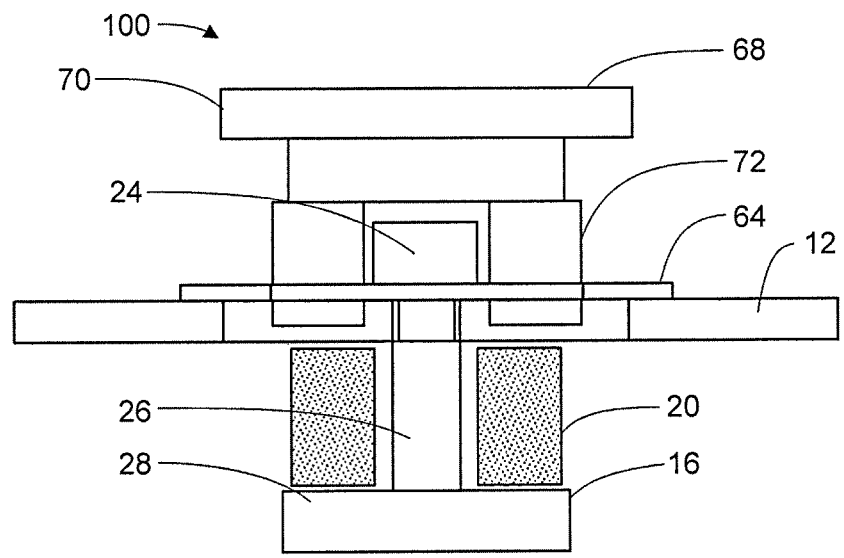
FIG. 7 is an illustration of a side view of an exemplary applicator device showing select features.

FIG. 7 shows another exemplary actuator or applicator 100. As seen in FIG. 7, a planar plate member or holder 12 has an upper or proximal surface 34 and a lower or distal surface 36. The plate member has an opening 82 extending at least partially through the plate. In one non-limiting embodiment is the opening is centrally located on the plate or located near the center of the plate. The plate member is typically rigid or substantially rigid. Preferably, the plate member is sufficiently rigid to constrain, along with a plunger distal end, the energy storage element as described further below.

In one embodiment, a flexure element 64 having a gap 66 is adjacent the upper or proximal surface 34 of the plate member. The flexure element may be retained at least partially within the opening of the plate member. The flexure element may be retained by or secured to the plate member by any suitable manner including, but not limited to, a mechanical feature such as a locking system, an adhesive, and/or by virtue of the shapes of the opening and the flexure element. The flexure element includes a gap capable of moving between a first position 74 (FIG. 13A) and a second position 76 (FIG. 13C). Preferably, the first position is smaller or constrained as compared to a larger or expanded second position. The gap of the flexure element is at least partially aligned with the opening 82 of the plate member. It will be appreciated that where the applicator does not include a flexure element, the opening of the plate member is capable of moving between a first and a second position. The flexure element typically has a planar region that at least partially overlies the proximal surface of the plate member. In embodiments, the flexure element overlies at least a portion of the plate opening. In further embodiments, the flexure element includes structure or elements that extend from a distal surface to engage with or contact at least a portion of the opening. In this manner, the flexure element is retained adjacent the opening.

Figure 11:
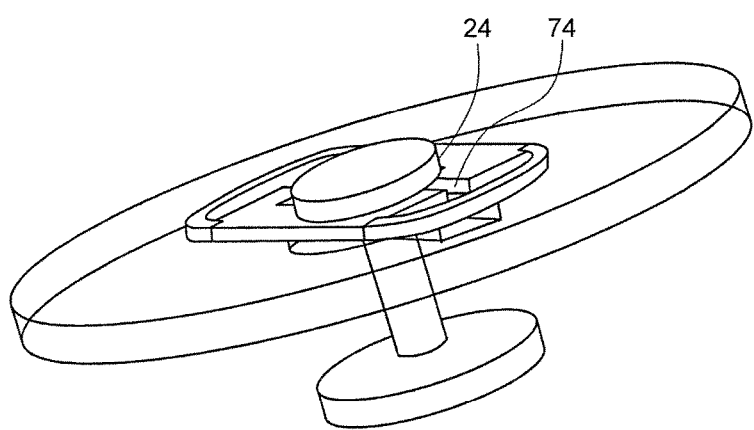
FIG. 11 is an illustration of an exemplary applicator device showing select features.

The applicator further includes a plunger 16 having a central post or shaft 26 and a proximal 24 and distal end 28. The proximal end of the plunger is preferably sized and shaped so that it is retained by the gap of the flexure element in the first position. It will be appreciated that the plunger may have any suitable shape or size. As shown in FIG. 7, one suitable shape comprises a cylindrical shaft and circular proximal and distal ends. It will be appreciated, however, that other shapes are suitable including, but not limited to a rectangular prism or other polygonal prisms. It will further be appreciated that the shaft, proximal end, and distal end may each have a different geometry. As one example, the shaft and proximal end may be cylindrical with the distal end having a square or rectangular shape. It will further be appreciated that one or both of the proximal and distal ends may be a plate having a circular, square, rectangular, elliptical or irregular shape. Preferably, the proximal end has a wider diameter than a diameter of the central shaft. As noted above, the gap of the flexure element is at least partially aligned with the opening of the plate member and the plunger is slidably disposed within the aligned gap and opening such that the distal end of the plunger may pass through the aligned opening and gap. In one embodiment, the proximal end of the plunger includes an edge, ledge or undercut that extends at least partially beyond the gap in the first position. In one embodiment, the proximal end of the plunger is dimensioned to be retained by the gap/opening in its first position by a ledge circumscribing the plunger shaft. Thus, at least a portion of the ledge, underside or the undercut of the proximal end of the plunger rests on a proximal surface of the flexure element and/or the plate member. Preferably, the proximal end is surrounded by the aligned opening and gap such that the proximal end is supported and retained by or on the proximal surface around or substantially around at least the edge of the proximal end. The proximal end may have any suitable size and shape. The proximal end is dimensioned so that it cannot pass through the gap and/or opening when the gap/opening is in the first position but passes through the gap/opening in the second position. FIG. 11 shows an exemplary embodiment with the plunger proximal end 24 retained by the gap in the first position. The actuating member and other features of the device are not included in the figure to better show the retained plunger proximal end.

Figure 12:
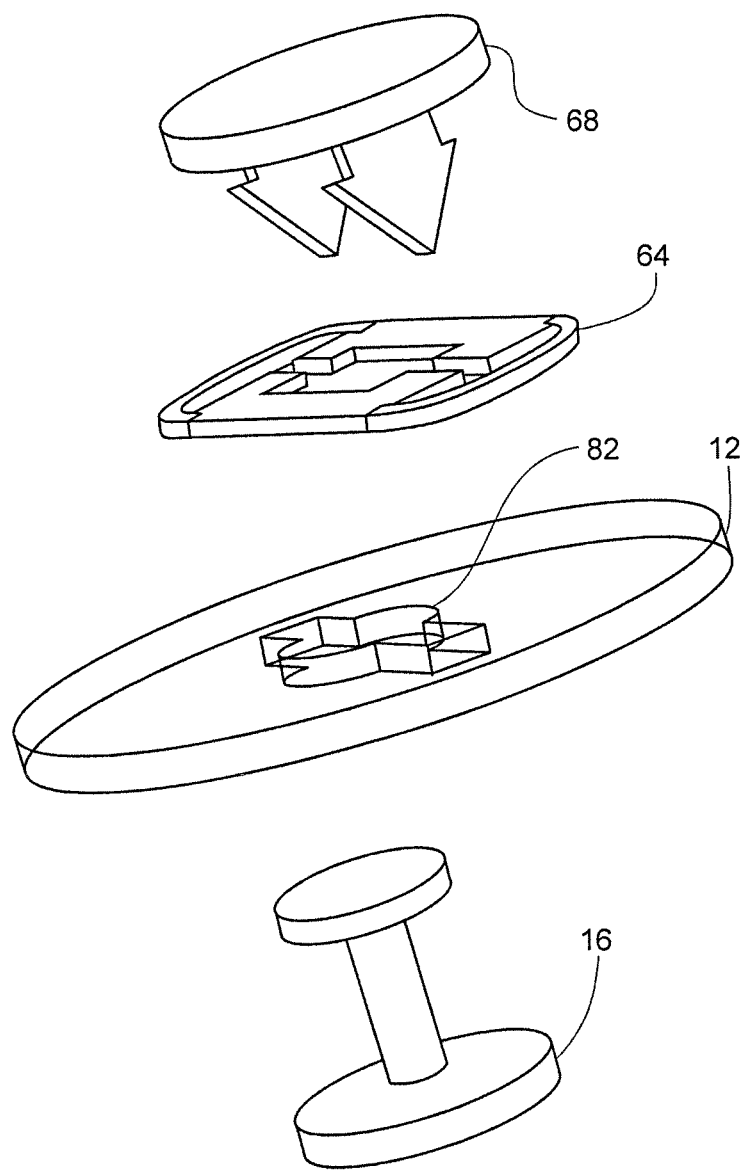
FIG. 12 is an exploded view of an exemplary applicator device showing select features.

FIG. 12 shows and exploded view of an actuating member 68, a flexure element 64, a plate 12, and a plunger 16 in exploded view. As seen in FIG. 12, the plate opening 82 may include a cut-out or other area large enough for the plunger proximal end to pass through when the gap is in the second position. It will further be appreciated that the opening may be wide enough at several or all points along its width for the plunger proximal end to pass through. Although the plunger proximal end is shown to be smaller in diameter than the plunger distal end, it will be appreciated that the ends may be the same diameter or the plunger distal end may have a smaller diameter than the proximal end.

The plate member, plunger, and flexure element may be formed of any suitable material. In one non-limiting embodiment, the plate member and/or flexure element and the plunger are at least partially formed of a material having an elastic modulus of between about 0.5-500 KSI. In embodiment, at least one of the plate member, the plunger, or the flexure element is formed of a metal including, but not limited to stainless steel, carbon steel, titanium, and alloys thereof. In one preferred embodiment, at least the flexure element, where present, and the plunger are formed of a metal.

The distal end of the plunger preferably includes a microprojection or microprojection array or other agent delivery device affixed or integral with a distalmost end or bottom surface 30 of the plunger distal end 28. The discussion of delivery devices above is applicable to this embodiment.

The applicator further comprises an actuating member 68 for moving the gap from the first position to the second position. The actuating member acts to move the gap and/or opening from the first position to the second position. As the gap/opening moves to the second position (or reaches the second position), the gap/opening becomes large or wide enough for the proximal end of the shaft to pass through and be released. Central pressure from the actuating member is preferably evenly distributed to the gap. The actuating member includes a proximal end 70 for receiving pressure and a distal end 72 for positioning at least partially in the gap/opening. The proximal end may have any shape suitable for receiving pressure including without limitation a button, pin, or plate. Typically, the pressure is a downward pressure in the direction from the proximal end of the actuator toward the distal end of the actuator (and typically toward the gap/opening). Pressure may be applied by any suitable means including manual or mechanical. Where the pressure is manually applied, the actuator proximal end has an external surface 78 that is suitable for contact by a user.

Figure 8:
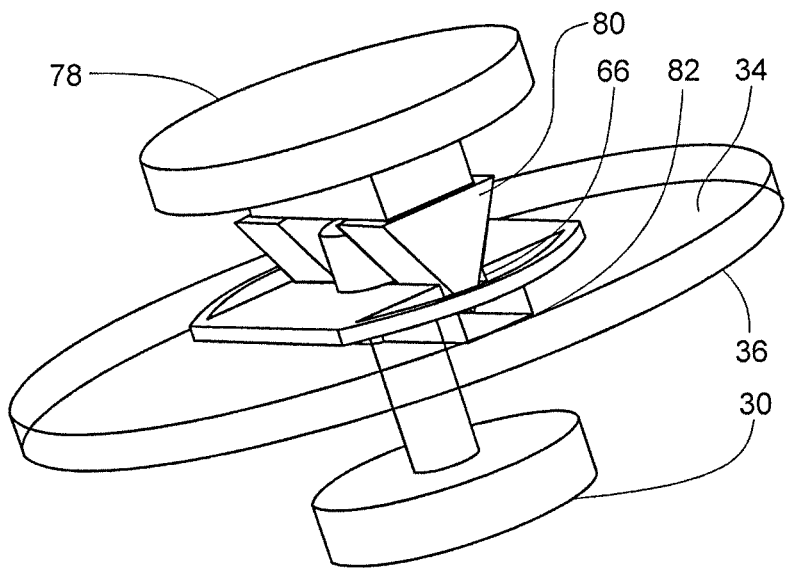
FIG. 8 is an illustration of an exemplary applicator device showing select features.

The actuator distal end has a shape suitable for moving or pushing the gap/opening from the first position to the second position. In the embodiment shown in FIG. 8, actuator distal end may be a polyhedral-shaped member 80. In embodiments, the polyhedral-shaped member has 2-8 faces. In one embodiment, the polyhedral-shaped member is sized and shaped such that a distal portion fits at least partially within the gap/opening when the gap/opening is in the first position. As pressure is applied to the proximal end of the actuator, the polyhedral-shaped member is pushed into the gap/opening and making it wider or open up to the second position. It will also be appreciated, however, that the polyhedral-shaped member may not contact or may be adjacent the gap/opening when the gap/opening is in the first position. In this embodiment, pressure applied to the proximal end of the actuator results in the polyhedral-shaped member first entering the gap/opening and then pushing it open or wider. In the embodiment shown in FIG. 8, the polyhedral-shaped member is a double incline wedge-shaped member. The wedge shape has the advantage of two sloping planes so that the gap/opening is opened on two surfaces or both sides simultaneously. The angular slopes of the wedge press with opposing forces on the spring flexure element increasing the gap/opening. Pressure on the actuator increases the gap where the undercut or ledge of the plunger proximal end rests until the undercut clears the gap/opening and the plunger is released.

The polyhedral-shaped member may include a gap, cut-out or area dimensioned to receive or fit around at least a portion of the proximal end of the plunger. In the embodiment shown in FIG. 8, the polyhedral-shaped member has a gap or opening allowing space for the plunger proximal end to rest on the flexure element. The shape of the gap or opening may be any shape suitable to receive the proximal end of the plunger. In non-limiting embodiments, the gap or opening in the polyhedral-shaped member is circular, oval, rectangular, square or other polyhedral shape. It will be appreciated that the shape of the gap or opening in the polyhedral-shaped member may be selected to accommodate the portion of the plunger proximal end therein. The gap or opening in the polyhedral-shaped member may have the same or different shape as the proximal end of the plunger. Further, the polyhedral-shaped member gap or opening may be any suitable dimension to receive the distal portion of the plunger.

The energy needed to actuate is that required to spread the gap and/or opening sufficiently to allow the plunger proximal end to pass through. This energy depends on their precise dimensions and the material characteristics (e.g., Young's modulus) of the material out of which they are made.

Figure 13A:
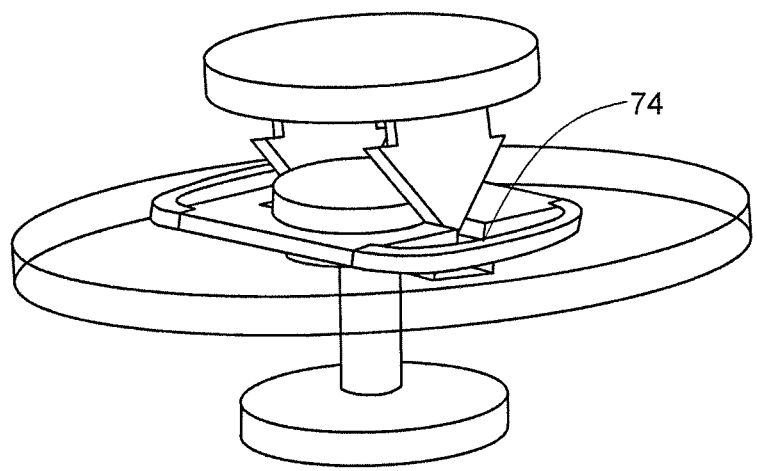
FIGS. 13A-13C are illustrations of an exemplary applicator device showing select features in use.
Figure 13B:
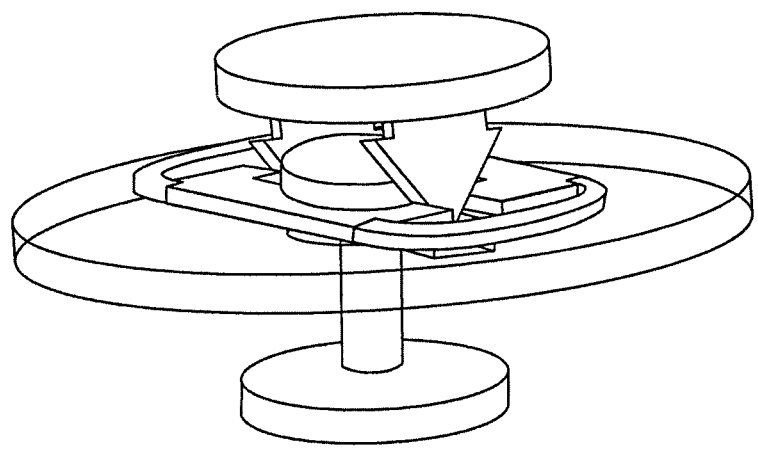
Figure 13C:
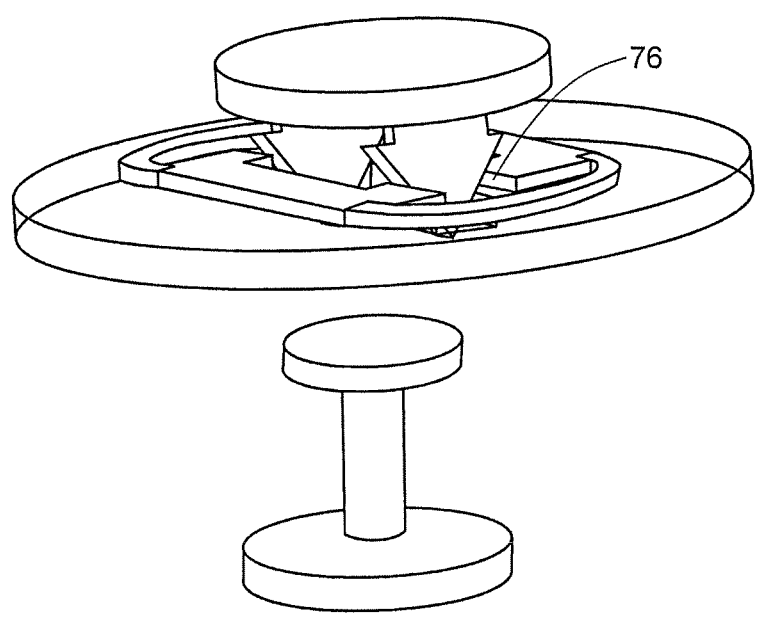

FIGS. 13A-13C show an exemplary use of devices described herein. FIG. 13A shows a portion of the device with the gap in the first position or at least in a position that retains the plunger proximal end. FIG. 13B shows expansion of the gap by application of force to the proximal surface of the actuating member. The actuating member acts on both or all sides of the gap to move the gap from the first position to the second position in which the plunger is passes through the gap/opening and is released as shown in FIG. 13C.

One problem with some prior microstructure arrays is uneven plunger movement during release of the plunger. These effects are undesirable as they lead to tilting or wobbling of the plunger within the housing during application. The plunger loses energy as it contacts or hits the housing, which reduces the energy available for penetrating skin with the microprotrusions. Another issue is that the plunger may tilt in the housing causing the microprotrusions to contact the skin at an angle rather than "straight" with a central axis of the microprotrusions being substantially perpendicular to the skin. With the present configurations, the distal portion of the plunger is released from the gap/opening at a single point of release. These configurations are advantageous because the release of the plunger occurs simultaneously or substantially simultaneously around the undercut or ledge. Thus, the release does not interfere with the direction of deployment of the plunger and the microprotrusion array is deployed in the intended direction with the intended force. The central release conserves energy required to release the plunger, results in consistent energy used to deploy the microstructures into the skin and/or requires lower energy as the microstructures are deployed into the skin at the correct angle.

Figure 9:
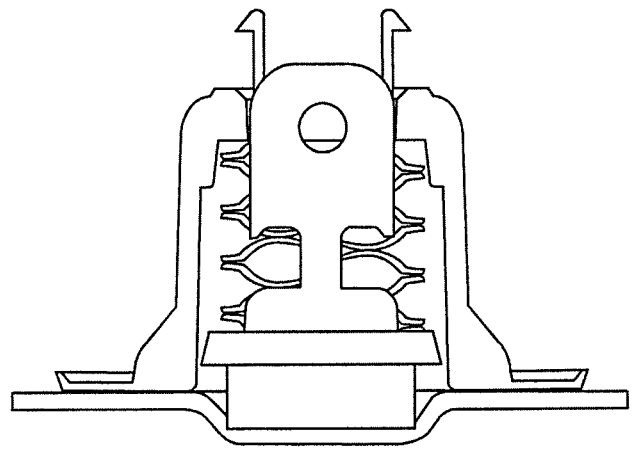
FIG. 9 is an illustration of an exemplary applicator device in a final, extended or equilibrium state.

It will be appreciated that once the plunger proximal end passes through the gap/opening, the gap/opening may return to the first position. In this embodiment, once the plunger proximal end passes through the gap/opening, and the gap/opening has returned to the first position, the proximal end of the plunger may rest against the under or distal surface of the plate and/or flexure element. It will be appreciated that the length of the plunger may be selected or adjusted to provide a desired position when released from the gap/opening. Where the device includes a housing, the length of the plunger may be selected so that a desired length of the plunger extends beyond the housing distal end. In embodiments, it is preferable for the plunger distal end with the microprotrusion array to extend beyond the skin surface at equilibrium. In further embodiments as shown in FIG. 9, the plunger has an extended final equilibrium position.

As seen in FIG. 7, the applicator further includes an energy storing element 20 positioned between an upper or proximal surface of the plunger distal end and a lower or distal surface of the plate member. Any suitable energy storing element is contemplated including, but not limited to springs or elastic components. The discussion of energy storing elements above is relevant to and considered as part of the present embodiment. When the plunger is retained by the gap/opening, the energy-storage member has a first force of stored energy, and when the plunger is released from the gap/opening, the energy-storage member releases its stored energy and in so doing moves the plunger. The energy storing element is typically maintained in a constrained or restrained position between the proximal surface of the plunger and the distal surface of the plate member when the plunger proximal end is retained by the gap/opening. When the plunger proximal end is released from the gap/opening, the energy storing element is released from the constrained position and the stored energy pushes the plunger distal end away from the plate and toward the patient's skin. It is generally desired to use the lowest appropriate energy in deploying microstructures to prevent uncomfortable sensations or pain in the subject and/or to prevent tissue damage from the impact.

The present embodiment may further include an outer housing 63 at least partially surrounding or enclosing the applicator. The discussion of a housing above is relevant to and included herein. Preferably at least part of the actuator is accessible or extends beyond the proximal end of the housing so that the user can apply pressure to the actuator. In another embodiment, the housing includes an actuator contacting area or element where the user applies pressure to the housing at the area or to the element that is transferred to the actuator proximal end. In another embodiment, the housing includes an opening at the proximal end for a user to access the actuator. The actuator proximal end may extend at least partially through the opening in the housing or the opening may be dimensioned so that a user may access the proximal end of the actuator through the opening.

As with the above embodiment, applicators contemplated herein will commonly have at least two states or configurations. In the first state or configuration, the proximal end of the plunger is retained by the plate member and/or flexure element. In the first state or configuration, the energy storing element is restrained in a high energy position between the plate element and the plunger distal end. This is typically expected to be the state of the applicator following manufacturing and during shipping and storage. When the plunger proximal end passes through the gap/opening, the energy storing element is released from the constrained state and releases all or a part of the stored energy. In this second state or configuration, which is arrived at by pressing or otherwise operating the actuating element, the microprojection array projects modestly outward from the applicator.

The materials from which the applicator components are manufactured can be selected from a wide variety known to a skilled artisan. For example, a filled polymer material is suitable for manufacture of the outer cover or housing, the flexure member and/or the actuating member. A skilled artisan will understand the various material properties to be considered when selecting a suitable material for each component part.

The applicators described in each of the embodiments described above can optionally include a safety mechanism or latch to prevent unintended actuation of the applicator and consequential deployment of the microneedle array. Various embodiments of a safety mechanism are described in U.S. Patent Publication No. 2011/0276027, which is incorporated herein in its entirety.

A problem with some prior applicators is the plunger is not deployed with sufficient energy or the plunger may bounce after contacting the skin or the skin may move away due to the impact. The skin may thus become separated from the microprotrusion array after the initial impact. Without a retaining force, the skin may separate at the end of the plunger's travel, continuing its motion as the plunger moves at a slower rate. While the microprotrusion array may later return to contact the skin as the plunger bounces, the individual microprotrusions will no longer be aligned with the holes created during the initial impact of the array with the skin and the plunger may not have sufficient energy to create new holes with the microprotrusions. Alternatively, some prior applicators suffer from the excessive application of force or displacement of the plunger. Excessive displacement or impact force of the plunger into the skin can cause uncomfortable sensations and pulling of the skin. Additionally, excessive compression of the skin can reduce fluid flow through the tissues surrounding the microprotrusion array, which slows dissolution of the therapeutic agent from the microprotrusions and the subsequent transport into the subject's system. Both of these problems may lead to the degradation of the drug product and/or improper or incomplete delivery of the therapeutic agent.

The proper contact of the microprotrusions with the skin may be achieved by adjusting the final equilibrium position of the plunger. In embodiments, the displacement of the plunger distal end is 0.03-0.2" below the surface of the subject's skin at equilibrium. In embodiments, the final displacement of the plunger of at least 0.030" as measured at plunger equilibrium in free air is desired. The "final displacement" refers to the extension of the plunger distal surface beyond the surface of the skin as shown in FIG. 9. This final displacement or the equilibrium position is determined by the length of the plunger and/or the equilibrium position of the energy storage member. In other embodiments, a final displacement is approximately 0.2". In a specific embodiment, the final displacement is 0.2" using a spring with 54 lb/in and a plunger having a diameter of approximately 0.6". In an embodiment, the length of the plunger shaft is selected such that it extends beyond the distalmost end of the housing at equilibrium. In another embodiment, the housing distal end includes a skin contacting surface and the length of the plunger shaft is selected such that the plunger extends beyond the skin contacting surface. In yet another embodiment, the plunger distal end extends below the skin surface at equilibrium. It will be appreciated the final displacement is dependent on the force required to depress the plunger from an extended state to flush with the housing. In an embodiment, the plunger travels a distance longer than the length of the plunger shaft. It will be appreciated that the length of the plunger shaft and/or the energy storing element may be selected to provide a force on the plunger that causes the plunger to travel a distance longer than the length of the shaft.

When the microprojections are dissolvable or erodible, a further advantage of an extended plunger equilibrium position is that the continued application of force allows the dissolvable microprojections to penetrate deeper into the skin as the microprojections dissolve. The biased force pressing the microprojections into the skin to the extended equilibrium position may further cause the microprojections to penetrate deeper into the skin as the distal tips dissolve.

Without being limited as to theory, maintaining pressure on the microprotrusions at equilibrium keeps the protrusion distal ends inserted in the skin. As the microprotrusions dissolve, the continued pressure pushes the protrusions deeper into the skin until the protrusions substantially or completely dissolve.

One problem with actuators using an energy storage element such as a spring or elastic element is that the energy storage element may exert forces on one or more components of the applicators, leading to dimensional distortion and/or creep over an extended period of time. These effects are undesirable as they lead to variations in the applicator geometry and a loss in the stored elastic energy over time. In one embodiment, at least the plate and plunger of the blocking element embodiment or the flexure member and the plunger of the opening release embodiment are formed of materials that do not exhibit creep. In one embodiment, at least the plate and plunger or the flexure member and the plunger are formed from a metal. Where the applicator does not include a flexure member, at least the plate member and the plunger may be formed from a metal or material that does not exhibit creep. Exemplary metals include, but are not limited to stainless steel, carbon steel, titanium, and alloys thereof. In this embodiment, all or most of the mechanical load from the energy storage element is borne by metal parts, which are not subject to dimensional distortion and creep over time. In another embodiment, at least the plate and plunger of the blocking element embodiment or the flexure member/plate and the plunger of the opening release embodiment are formed from a plastic or polymer that does not exhibit creep and/or dimensional distortion at a given stress level. In this embodiment, all or most of the mechanical load from the energy storage element is borne by parts formed from materials which are not subject to dimensional distortion and creep over time. Reducing the dimensional distortion and creep leads to maintaining the same stored elastic energy for an extended period of time. Maintaining the same or similar stored elastic energy over a period of time is important for having an extended shelf life of at least preferably about 6 months, more preferably about 12 months, and most preferably about 24 months. In further embodiments, the same stored elastic energy is maintained over a shelf life of at least about 1-10 years. In specific, but not limiting embodiments, the same or similar stored elastic energy is maintained over a shelf life of at least about 1 year, about 2 years, about 3 years, about 4 years, about 5 years, or about 10 years or longer.

Another issue or problem with current microstructure or microneedle arrays arises with extended use or wear of the applicators. Wearing a potentially bulky applicator for an extended period of time is inconvenient during normal activities or exercising. Another potential problem is that the microneedle arrays may bounce off the skin and cause poor drug delivery. Furthermore, another potential problem is the microneedle array may pull out of the skin after impact into the skin also causing poor drug delivery. In some embodiments, it is desirable for the microstructure array or other delivery device to be removable from the applicator. This embodiment provides for a low profile and/or more comfortable delivery device that can be worn for longer or extended periods of time.

Figure 4:
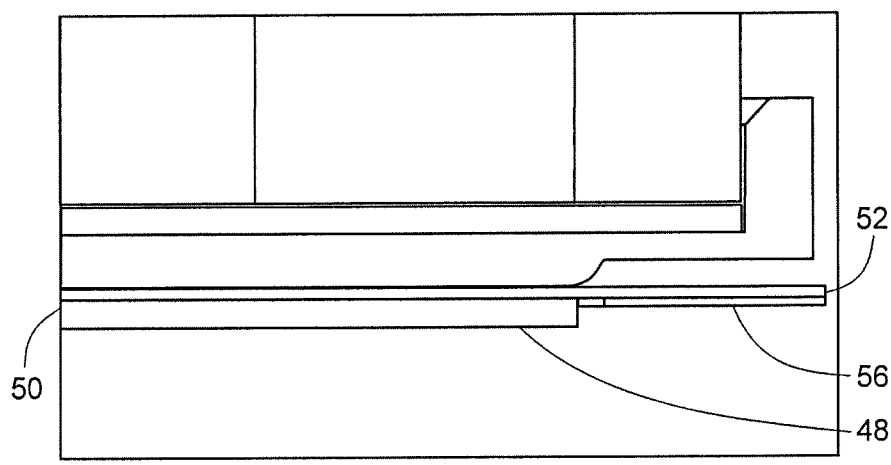
FIG. 4 is an illustration of a side view of an exemplary applicator device showing select features.
Figure 5A:
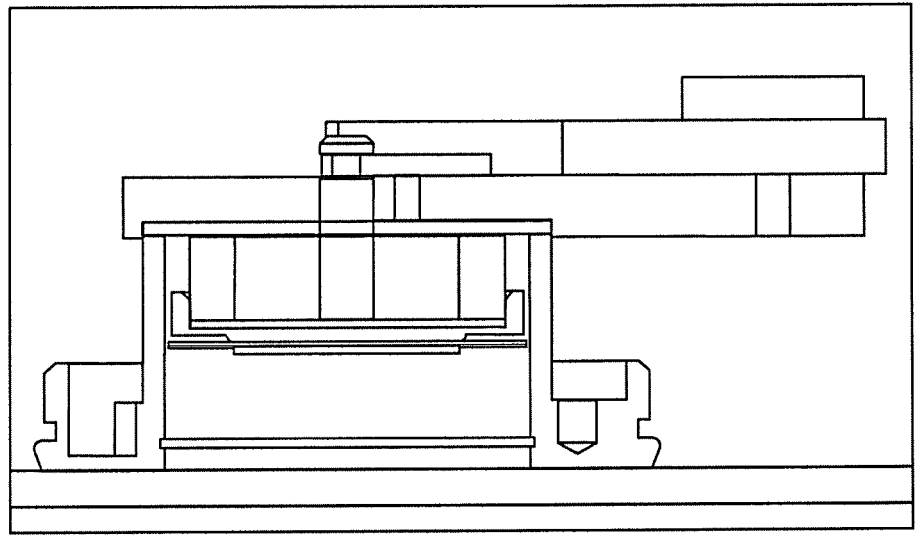
FIGS. 5A-5C are side view illustrations of an exemplary applicator device in use.
Figure 5B:
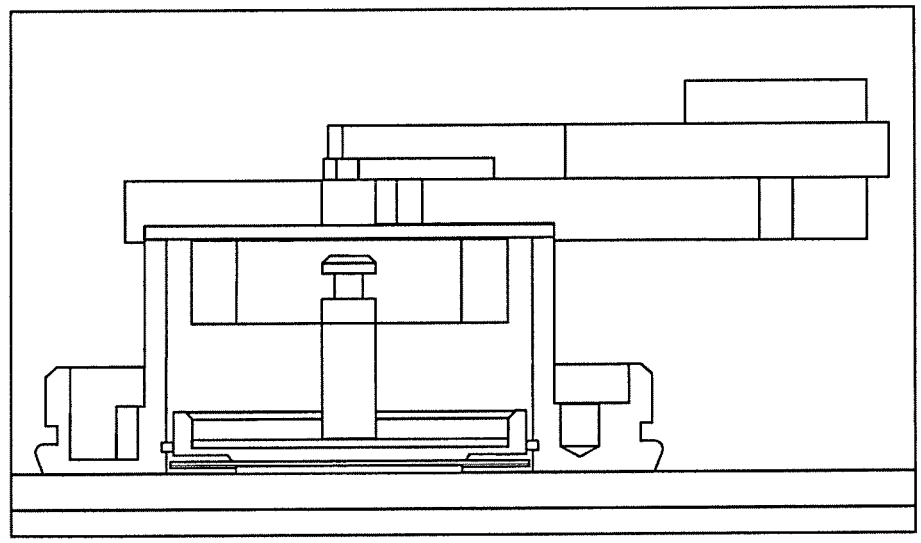
Figure 5C:
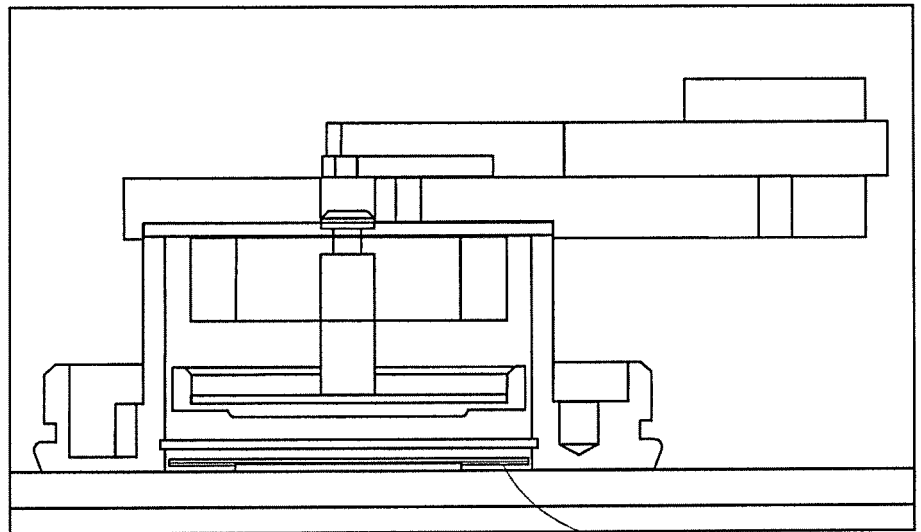

In one embodiment, the present applicators may include a backing assembly that is removable from the applicator. In one embodiment as shown in FIG. 4, a backing assembly 50 may include a support layer 52, a microstructure array or other delivery device 48, and an adhesive 56 positioned at least partially around the microstructure array or delivery device. In one embodiment, the adhesive is positioned as a ring around the microstructure array. The backing assembly is initially attached or placed in close proximity to the plunger or the applicator. Preferably, the backing assembly is attached or affixed to the distal surface of the plunger. Upon activation of the applicator, the plunger is released which deploys or forces the microstructures into the skin. The backing assembly with the adhesive ring at least partially adheres to the skin, allowing the applicator to detach from the skin with the microstructures of the array being deployed at least partially in the subject's skin. Another advantage of a backing assembly is that the microstructures are prevented from pulling out of the skin as the skin tissue relaxes for extended wear durations (e.g. ≤5 minutes). Additionally, this configuration prevents microstructures from pulling out due to the plunger bouncing off the skin after impact. The backing assembly preferably detaches from the plunger immediately after impact, and the adhesive ring on the backing assembly holds the microstructure array onto the skin. The plunger bounces upward and separates from the backing assembly or the backing assembly separates from the plunger when the applicator is removed. The backing assembly with the microstructure array stays on the skin. Any suitable adhesive for adhering the backing assembly may be used including those described with reference to the skin contacting area. In an embodiment, the adhesive has sufficient adhesion to the skin to retain the microstructure array on the subject's skin when the plunger bounces away from the skin or when the applicator is removed from the subject's skin. The support layer may be formed of any suitable material including, but not limited to, polymers and metals. In an embodiment, at least the areas of the support that contact the subject's skin are biocompatible. The support layer may be rigid, semi-rigid or flexible. In one embodiment, the support layer is flexible enough to conform to the skin application site. FIGS. 5A-5C show an exemplary applicator including a backing assembly in operation. In this embodiment, the applicator with the plunger retained by the blocking member is first placed against a subject's skin (FIG. 5A). The backing assembly is positioned on the distalmost surface of the plunger distal end. The applicator is actuated and the blocking member releases the plunger, which is deployed downward toward the patient's skin (FIG. 5B). The microstructure array on the distal end of the plunger is deployed or driven such that at least a portion of the microstructures in the array at least partially pierce or penetrate the subject's skin. As seen in FIG. 5C, the plunger bounces or otherwise moves vertically away from the skin and the backing assembly detaches from the plunger to remain on the subject's skin.

Figure 6:
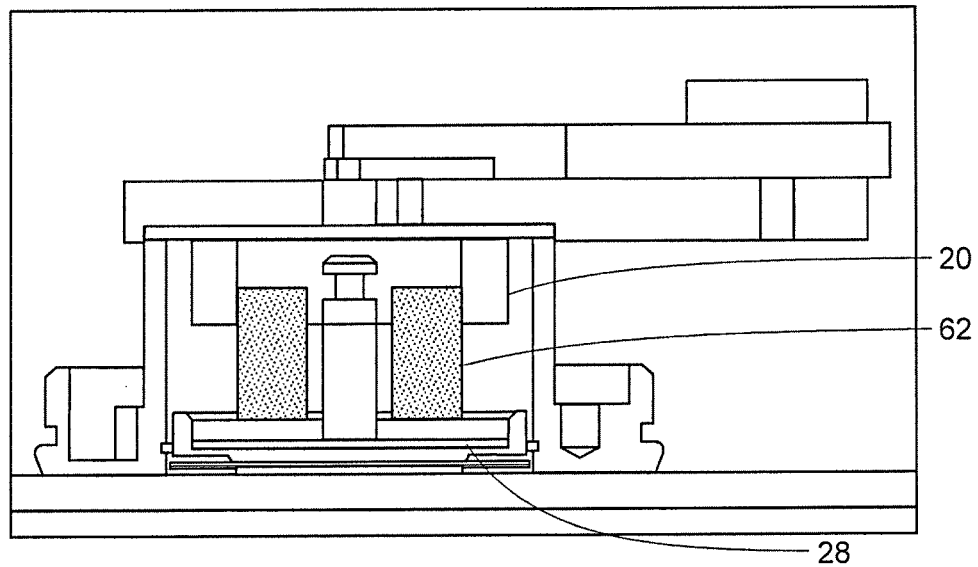
FIG. 6 is an illustration of a side view of an exemplary applicator device.

In one embodiment, the applicators may include a damper to dampen the bounce, upward or vertical motion of the plunger away from a subject. The plunger damper changes the system dynamics from under-damped to critically or over-damped. In non-limiting embodiments, a foam, friction material, or viscous material is placed in mechanical communication with the plunger and the energy storing element to act as a plunger damper. The plunger damper's function is to provide an energy loss to minimize plunger bounce (vertical upward motion) after the applicator is activated and the plunger strikes the skin. In one embodiment as shown in FIG. 6, the damper 62 is positioned between the energy storing device 20 and the plunger distal end 28. When the plunger is released from the blocking member, the plunger deploys and the damper expands to at least partially fill any open space between the energy storing device and the plunger distal end.

It will be appreciated that elements and/or embodiments described above with reference to one applicator embodiment are applicable to all applicator embodiments described. Discussion of common elements between the embodiments is intended to apply to all embodiments. In particular, but without limitation, discussion of the plate, actuating member, plunger, delivery devices, energy-storage element, and housing with reference to one embodiment is intended to also apply to other embodiments.

III. Methods of Use

In another aspect, a method for administering an active agent or therapeutic agent to a subject is provided. Preferably, the active or therapeutic agent is administered dermally, transdermally, mucosally, and/or transmucosally. The method comprises providing a microprojection array or other delivery device in conjunction with any one of the applicators described herein, the microprojection array or delivery device comprising at least one active agent. Preferably, the microprojection array or other delivery device is configured to deliver at least one therapeutic agent. The agent may be coated on at least a portion of the microprojections and/or contained within at least a portion of the microstructures. The agent is delivered dermally, transdermally, mucosally, or transmucosally by actuation of the applicator, to deploy the microprojection array into contact with the skin, or more generally a membrane or body surface, of a subject. The active agent to be administered can be one or more of any of the active agents known in the art, and include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof. In embodiments the therapeutic agent is a protein or a peptide. In another embodiment, the agent is a vaccine.

Non-limiting examples of peptides and proteins which may be used with microprotrusion arrays include, but are not limited to parathyroid hormone (PTH), oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumor necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof. Administration of oligonucleotides is also contemplated, and includes DNA and RNA, other naturally occurring oligonucleotides, unnatural oligonucleotides, and any combinations and/or fragments thereof. Therapeutic antibodies include Orthoclone OKT3 (muromonab CD3), ReoPro (abciximab), Rituxan (rituximab), Zenapax (daclizumab), Remicade (infliximab), Simulect (basiliximab), Synagis (palivizumab), Herceptin (trastuzumab), Mylotarg (gemtuzumab ozogamicin), CroFab, DigiFab, Campath (alemtuzumab), and Zevalin (ibritumomab tiuxetan).

In other embodiments, at least a portion of the distal layer comprises an agent suitable for use as a prophylactic and/or therapeutic vaccine. In an embodiment, the vaccine comprises an antigen epitope conjugated on or to a carrier protein. It will be appreciated that vaccines may be formulated with our without an adjuvant. Suitable vaccines include, but are not limited to, vaccines for use against anthrax, diphtheria/tetanus/pertussis, hepatitis A, hepatitis B, Haemophilus influenzae type b, human papillomavirus, influenza, Japanese encephalitis, measles/mumps/rubella, meningococcal diseases (e.g., meningococcal polysaccharide vaccine and meningococcal conjugate vaccine), pneumococcal diseases (e.g., pneumococcal polysaccharide vaccine and meningococcal conjugate vaccine), polio, rabies, rotavirus, shingles, smallpox, tetanus/diphtheria, tetanus/diphtheria/pertussis, typhoid, varicella, and yellow fever.

In another embodiment, at least a portion of the distal layer comprises an agent suitable for veterinary uses. Such uses include, but are not limited to, therapeutic and diagnostic veterinary uses.

In operation, and with reference again to FIGS. 13A-13C, an applicator comprising an energy-storage element is placed in contact with the skin such that a skin contacting surface directly contacts the external skin surface (stratum corneum) and, optionally, is adhered to skin by means of adhesive disposed on the skin contacting surface. The gap of the flexure element is in the first position with the proximal end of the plunger retained by the gap. The energy-storage element is in a first, constrained state and is movable to a second extended or unrestrained state or configuration. The actuating member is pressed downward causing the distal end of the actuating member to move downward, engaging the gap of the flexure element and pushing the inner edges of the gap to move from the first position to a second wider or open position. When in the gap is in the second position, the plunger proximal end that had been retained by the flexure element passes through the gap/opening and is released. Release of the plunger from the flexure element also releases the energy-storage element to travel from the restrained or compressed position to an extended position. As a result of movement of the energy-storage member, a microarray in contact with the plunger distal end comes forcibly into contact with skin. In one embodiment, the plunger after release from the gap has an equilibrium position such that the distal end of the plunger on which the microprotrusion array is affixed is positioned below a surface of the skin.

IV. Examples

The following examples are illustrative in nature and are in no way intended to be limiting.

Example 1

Administration of a Microstructure Array with Blocking Element Release

An applicator comprising a microstructure array is applied to a subject's skin. The applicator includes a blocking member that retains a plunger proximal end by being at least partially inserted into a cut-out in the plunger proximal end. The actuator is moved in a pressed down such that the angular slopes of the attached polyhedral-shaped member press with opposing forces on the flexure element increasing the width of a gap in the flexure member. The actuator is moved into contact with the blocking member to rotate the blocking member away from contact with the plunger proximal end until the plunger cut-out clears the blocking member and the plunger is released. The plunger is moved toward the subject's skin by expansion of a spring placed between a plate and the plunger distal end. The plunger impacts the skin and the microstructure array pierces or ruptures the skin surface.

Example 2

Administration of a Microstructure Array with Opening Release

An applicator comprising a microstructure array is applied to a subject's skin. The actuator is pressed down such that the angular slopes of the attached polyhedral-shaped member press with opposing forces on the flexure element increasing the width of a gap in the flexure member. The actuator is pressed until the gap width increases until the undercut of a plunger central post rests clears the flexure element gap and the plunger is released. The plunger is moved toward the subject's skin by expansion of a spring placed between the flexure element and the plunger distal end. The plunger impacts the skin and the microstructure array pierces or ruptures the skin surface.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

1. An applicator, comprising:
   a rigid plate member with an upper surface and a lower surface, the plate member having at least one opening;
   a blocking element in contact with the upper surface of the plate member and being capable of moving between a first position and a second position;
   a plunger having a proximal end, a distal end on which at least one microprojection can be retained, and a shaft extending therebetween, the proximal end being at least partially retained by the blocking element in its first position;
   an energy-storing element positioned between the lower surface of the plate member and the distal end of the plunger; and
   an actuating member having an external surface for application of a force, and having at least one surface in mechanical communication with the blocking element, wherein the actuating member moves the blocking element from its first position to its second position when a force is applied to the external surface of the actuating member, thereby to effect release of the energy-storing element.

2. The applicator of embodiment 1, further comprising:
   at least one microprojection positioned on a bottom surface of the plunger distal end.

3. The applicator of the combined or separate embodiments 1 and 2, further comprising:
   at least one flexure element in mechanical communication with the blocking element, wherein the flexure element directs the blocking element into the plunger in the blocking member's first position.

4. The applicator of the combined or separate embodiments 1-3, wherein the actuating member causes the blocking element to have a linear displacement.

5. The applicator of the combined or separate embodiments 1-4, wherein the actuating member causes the blocking element to have a rotational displacement.

6. The applicator of the combined or separate embodiments 1-5, wherein the energy-storing element is an elastic energy element.

7. The applicator of the combined or separate embodiments 1-6, wherein the elastic energy element is selected from a compression spring, a coil spring, or a wave spring.

8. The applicator of the combined or separate embodiments 1-7, wherein the proximal end of the plunger is dimensioned to be retained by the blocking element in its first position by a ledge at least partially circumscribing the plunger shaft.

9. The applicator of the combined or separate embodiments 1-8, wherein the at least one opening has a shape selected from circular, oval, rectangular, and square.

10. The applicator of the combined or separate embodiments 1-9, wherein at least the plate member and the plunger are formed from material with an elastic modulus between about 0.5 to 500 KSI.

11. The applicator of the combined or separate embodiments 1-10, wherein at least the plate member and the plunger are formed from a metal.

12. The applicator of the combined or separate embodiments 1-11, wherein at least the blocking element is formed from a material with an elastic modulus between about 0.5 to 500 KSI.

13. The applicator of the combined or separate embodiments 1-12, wherein the blocking element is formed from a metal.

14. The applicator of the combined or separate embodiments 1-13, wherein the metal is selected from stainless steel, carbon steel, titanium, and alloys thereof.

15. The applicator of the combined or separate embodiments 1-14, further comprising a housing member with an opening through which the external surface of the actuating member can be accessed.

16. The applicator of the combined or separate embodiments 1-15, wherein the housing opening is sized to receive at least a part of the external surface of the actuating member.

17. The applicator of the combined or separate embodiments 1-16, wherein the plunger shaft has a length and the energy-storing element is selected to provide a force on the plunger that causes the plunger to travel a distance longer than the length of the shaft.

18. The applicator of the combined or separate embodiments 1-17, wherein the housing includes a surface on which an adhesive is or can be applied, to secure the housing to a subject.

19. The applicator of the combined or separate embodiments 1-18, wherein the length of the plunger shaft is such that it extends beyond the surface on which the adhesive is or can be applied.

20. The applicator of the combined or separate embodiments 1-19, wherein the at least one microprojection is a microprojection array, a hypodermic needle or a trocar.

21. The applicator of the combined or separate embodiments 1-20, wherein the microprojection array comprises a plurality of dissolvable or erodible microprojections.

22. The applicator of the combined or separate embodiments 1-21, wherein the at least one microprojection includes at least one therapeutic agent.

23. The applicator of the combined or separate embodiments 1-22, wherein at least a portion of the plurality of microprojections are detachable from the microprojection array.

24. The applicator of the combined or separate embodiments 1-23, further comprising a backing member positioned on a distal surface of the plunger distal end, wherein the backing member comprises the at least one microprojection;
   the backing member being detachable from the plunger distal end.

25. The applicator of the combined or separate embodiments 1-24, wherein the backing member comprises a support layer adjacent the distal surface of the plunger distal end and an adhesive layer, wherein the at least one microprojection is positioned distal to the adhesive layer.

26. The applicator of the combined or separate embodiments 1-25, wherein the at least one microprojection is a microprojection array positioned distal to the adhesive layer.

27. The applicator of the combined or separate embodiments 1-26, wherein the adhesive layer at least partially surrounds the at least one microprojection.
28. The applicator of the combined or separate embodiments 1-27, further comprising:
    a damper positioned between the energy-storing element and a proximal surface of the plunger distal end.
29. A method of delivering a therapeutic agent to a subject, comprising:
    applying to a skin site of the subject, a microprojection array affixed to the distal end of the plunger of the applicator according to the combined or separate embodiments 1-28;
    contacting the external surface of the actuating member to actuate the actuating member from a first position to a second position in mechanical communication with the blocking element;
    moving the blocking element from its first position in contact with the proximal end of the plunger to its second position, whereby the plunger is released from contact with the blocking member;
    releasing the energy-storing element thereby to deploy the plunger into contact with a subject's skin; and
    delivering the therapeutic agent from the microprojection array to the subject.
30. The method of embodiment 29, further comprising: adhering the applicator to the subject's skin.
31. The method of the combined or separate embodiments 29-30, wherein moving the blocking element effects movement of the plunger from a retracted position to a deployed position.
32. The method of the combined or separate embodiments 29-31, wherein in the deployed position, the plunger has an equilibrium position such that the distal end of the plunger on which the microprojection array is affixed is positioned below a surface of the skin.
33. The method of the combined or separate embodiments 29-32, wherein the equilibrium position is about 0.03-0.2 inches below the surface of the skin of the subject.
34. The method of the combined or separate embodiments 29-33, further comprising detaching a backing member such that the backing member and the microprotrusion array are retained on the subject's skin.
35. An applicator, comprising:
    a planar plate member with an upper surface and a lower surface, the plate member having at least one opening;
    a planar flexure element in contact with the upper surface of the plate member, the flexure element (i) having a gap capable of moving between first and second positions and (ii) being positioned to align the gap with the opening in the plate member;
    a plunger slidably disposed within the aligned gap and opening, the plunger having a shaft with a distal end on which at least one microstructure can be retained and a proximal end dimensioned such that the proximal end is retained by the gap in its first position and passes through the gap in its second position;
    an energy-storing element positioned between the lower surface of the plate member and the distal end of the plunger; and
    an actuating member having an external surface and a polyhedral-shaped member, the polyhedral-shaped member dimensioned to move the gap between its first and second positions when the external surface of the actuating member is contacted with sufficient force to effect release of the energy-storing element.
36. The applicator of embodiment 35, wherein the energy-storing element is an elastic energy element.
37. The applicator of the combined or separate embodiments 35-36, wherein the elastic energy element is selected from a compression spring, a coil spring, and a wave spring.
38. The applicator of the combined or separate embodiments 35-37, wherein the proximal end of the plunger is dimensioned to be retained by the gap in its first position by a ledge at least partially circumscribing the plunger shaft.
39. The applicator of the combined or separate embodiments 35-38, wherein the polyhedral-shaped member comprises between 2-8 faces.
40. The applicator of the combined or separate embodiments 35-39, wherein the polyhedral-shaped member has a gap dimensioned to receive the proximal end of the plunger.
41. The applicator of the combined or separate embodiments 35-40, wherein the plate opening has a shape selected from circular, oval, rectangular, and square.
42. The applicator of the combined or separate embodiments 35-41, wherein the plate opening is centrally located on the plate.
43. The applicator of the combined or separate embodiments 35-42, wherein at least the flexure element and the plunger are formed from a material having an elastic modulus between about 0.5 to 500 KSI.
44. The applicator of the combined or separate embodiments 35-43, wherein the material is a metal.
45. The applicator of the combined or separate embodiments 35-44, wherein the metal is selected from stainless steel, carbon steel, titanium, and alloys thereof.
46. The applicator of the combined or separate embodiments 35-45, further comprising a housing member with an opening through which the external surface of the actuating member can be received.
47. The applicator of the combined or separate embodiments 35-46, wherein the plunger shaft has a length and the energy-storing element is selected to provide a force on the plunger that causes the plunger to travel a distance longer than the length of the shaft.
48. The applicator of the combined or separate embodiments 35-47, wherein the housing includes a surface on which an adhesive is or can be applied, to secure the housing to a subject.
49. The applicator of the combined or separate embodiments 35-48, wherein the length of the plunger shaft is such that it extends beyond the surface on which the adhesive is or can be applied.
50. The applicator of the combined or separate embodiments 35-49, wherein the at least one microprojection is a microprojection array, a hypodermic needle or a trocar.
51. The applicator of the combined or separate embodiments 35-50, wherein the microprojection array comprises a plurality of dissolvable or erodible microprojections.
52. The applicator of the combined or separate embodiments 35-51, wherein the plurality of microprojections include a therapeutic agent.
53. The applicator of the combined or separate embodiments 35-52, wherein at least a portion of the plurality of microprojections are detachable from the microprojection array.

54. The applicator of the combined or separate embodiments 35-53, further comprising a backing member positioned on a distal surface of the plunger distal end, wherein the backing member comprises the at least one microprojection;
the backing member being detachable from the plunger distal end.
55. The applicator of the combined or separate embodiments 35-54, wherein the backing member comprises a support layer adjacent a distal surface of the plunger distal end and an adhesive layer, wherein the at least one microprojection is positioned distal to the adhesive layer.
56. The applicator of the combined or separate embodiments 35-55, wherein the at least one microprojection is a microprojection array positioned distal to the adhesive layer.
57. The applicator of the combined or separate embodiments 35-56, wherein the adhesive layer at least partially surrounds the at least one microprojection.
58. The applicator of the combined or separate embodiments 35-57, further comprising:
a damper positioned between the energy-storing element and a proximal surface of the plunger distal end.
59. A method of delivering a therapeutic agent to a subject, comprising:
applying to a skin site of the subject, a microprojection array affixed to the distal end of the plunger of the applicator according to the combined or separate embodiments 35-58;
contacting the external surface of the actuating member to actuate the actuator from a first position to a second position, whereby the flexure element gap is moved from its first position to its second position and releasing the plunger from a restrained position to a deployed position in contact with the subject's skin; and
delivering the therapeutic agent from the microprojection array to the subject.
60. The method of embodiment 59, further comprising:
adhering the applicator to the subject's skin.
61. The method of the combined or separate embodiments 59-60, wherein the microprojection array comprises a plurality of microprojections, and in the deployed position, the plunger has an equilibrium position such that the distal end of the plunger on which at least a portion of the plurality of microprojections are positioned below the surface of the skin.
62. The method of the combined or separate embodiments 59-61, wherein the equilibrium position is about 0.03-0.2 inches below the surface of the skin of the subject.
63. The method of the combined or separate embodiments 59-62, wherein deploying the plunger further comprises detaching the backing member such that the backing member and the microprotrusion array is retained on the subject's skin.
64. The applicator of the combined or separate embodiments of 1-28, wherein the therapeutic agent is selected from a drug, a small molecule, a protein or peptide, or a vaccine.
65. The method of the combined or separate embodiments of 29-34, wherein the therapeutic agent is selected from a drug, a small molecule, a protein or peptide, or a vaccine.
66. The applicator of the combined or separate embodiments of 35-58, wherein the therapeutic agent is selected from a drug, a small molecule, a protein or peptide, or a vaccine.
67. The method of the combined or separate embodiments of 59-63, wherein the therapeutic agent is selected from a drug, a small molecule, a protein or peptide, or a vaccine.

What is claimed is:
1. An applicator, comprising:
a rigid planar plate member with an upper surface on a first side of the plate member and a lower surface on a second side of the plate member, the plate member having at least one opening therethrough;
a blocking element in contact with the upper surface of the plate member and being capable of moving between a first position and a second position;
a plunger having a proximal end, a distal end on which at least one microprojection is retained, and a shaft extending therebetween, at least a portion of the proximal end rests directly on and is at least partially retained by the blocking element in its first position; wherein, the plunger is slidably accommodated within the opening of the plate member;
an energy-storing element positioned between the lower surface of the plate member and the distal end of the plunger; and
an actuating member having an external surface for application of a force, and having at least one surface in mechanical communication with the blocking element, wherein the actuating member moves the blocking element from its first position to its second position when a force is applied to the external surface of the actuating member, thereby to effect release of the plunger and the energy-storing element.
2. The applicator of claim 1, further comprising:
at least one microprojection positioned on a bottom surface of the plunger distal end.
3. The applicator of claim 2, wherein the at least one microprojection is a microprojection array comprising a plurality of microprojections, a hypodermic needle or a trocar.
4. The applicator of claim 3, wherein the plurality of microprojections are dissolvable or erodible microprojections.
5. The applicator of claim 2, wherein the at least one microprojection includes at least one therapeutic agent selected from a drug, a small molecule, a protein, a peptide, or a vaccine.
6. The applicator of claim 2, further comprising:
a backing member positioned on a distal surface of the plunger distal end, wherein the at least one microprojection is positioned on a distal surface of the backing member;
the backing member being detachable from the plunger distal end.
7. The applicator of claim 3, wherein at least a portion of the plurality of microprojections are detachable from the microprojection array.
8. The applicator of claim 1, further comprising:
at least one flexure element in mechanical communication with the blocking element, wherein the at least one flexure element directs the blocking element into the plunger in the blocking member's first position.

9. The applicator of claim 1, wherein the actuating member causes the blocking element to have a displacement selected from a linear displacement and a rotational displacement.

10. The applicator of claim 1, wherein the energy-storing element is an elastic energy element.

11. The applicator of claim 10, wherein the elastic energy element is selected from a compression spring, a coil spring, or a wave spring.

12. The applicator of claim 1, wherein the proximal end of the plunger is dimensioned to be retained by the blocking element in its first position by a ledge at least partially circumscribing the plunger shaft.

13. The applicator of claim 1, wherein at least one of the plate member, the blocking member, or the plunger are formed from a material with an elastic modulus between about 0.5 to 500 KSI.

14. The applicator of claim 1, wherein at least one of the plate member, the plunger, or the blocking member is formed from a metal.

15. The applicator of claim 14, wherein the metal is selected from stainless steel, carbon steel, titanium, and alloys thereof.

16. The applicator of claim 1, further comprising a housing member with an opening through which the external surface of the actuating member can be accessed.

17. The applicator of claim 16, wherein the housing includes a surface on which an adhesive is applied to secure the housing to a subject.

18. The applicator of claim 1, wherein the plunger shaft has a length and the energy-storing element is selected to provide a force on the plunger that causes the plunger to travel a distance longer than the length of the shaft.

19. The applicator of claim 1, further comprising:
a damper positioned between the energy-storing element and a proximal surface of the plunger distal end.

20. A method of delivering a therapeutic agent to a subject, comprising:
applying to a skin site of the subject, a microprojection array affixed to the distal end of the plunger of the applicator according to claim 1;
contacting the external surface of the actuating member to actuate the actuating member from a first position to a second position in mechanical communication with the blocking element;
moving the blocking element from its first position in contact with the proximal end of the plunger to its second position, whereby the plunger is released from contact with the blocking member;
releasing the energy-storing element thereby to deploy the plunger into contact with a subject's skin; and
delivering the therapeutic agent from the microprojection array to the subject.

21. The method of claim 20, further comprising:
adhering the applicator to the subject's skin.

22. The method of claim 20, wherein moving the blocking element effects movement of the plunger from a retracted position to a deployed position.

23. The method of claim 20, further comprising;
detaching a backing member from the plunger such that the backing member and the microprojection array are retained on the subject's skin when the applicator is removed from the subject's skin.

* * * * *